(12) United States Patent
Nebolsin et al.

(10) Patent No.: US 8,940,780 B2
(45) Date of Patent: Jan. 27, 2015

(54) N-ACYLIC AMINOACID DERIVATIVES, METHOD FOR THE PRODUCTION THEREOF, PHARMACOLOGICAL COMPOSITION AND THE USE IN THE FORM ANTI-ALLERGIC, ANTI-INFLAMMATORY AND HYPOLIPIDEMIC AGENTS

(75) Inventors: Vladimir Evgenievich Nebolsin, Moscow (RU); Tatyana Alexandrovna Kromova, Kaluga (RU); Galina Alexandrovna Zheltukhina, Moscow (RU); Violetta Leonidovna Kovaleva, Moscow (RU)

(73) Assignees: Otkrytoe Aktsionernoe Obschestvo Otechestvennye Lekarstva, Moscow (RU); Vladimir Evgenievich Nebolsin, Moscow (RU)

( * ) Notice: Subject to any disclaimer, the term of this patent is extended or adjusted under 35 U.S.C. 154(b) by 666 days.

(21) Appl. No.: 11/917,598

(22) PCT Filed: Jun. 15, 2006

(86) PCT No.: PCT/RU2006/000311
§ 371 (c)(1),
(2), (4) Date: Jul. 15, 2008

(87) PCT Pub. No.: WO2006/135280
PCT Pub. Date: Dec. 21, 2006

(65) Prior Publication Data
US 2008/0319040 A1    Dec. 25, 2008

(30) Foreign Application Priority Data
Jun. 15, 2005 (RU) .................. 2005118635

(51) Int. Cl.
*C07D 209/20* (2006.01)
*C07D 233/64* (2006.01)
(52) U.S. Cl.
CPC ............ *C07D 233/64* (2013.01); *C07D 209/20* (2013.01)
USPC .......... 514/399; 514/415; 548/338.1; 548/507
(58) Field of Classification Search
USPC .............................. 548/338.1, 507
See application file for complete search history.

(56) References Cited

FOREIGN PATENT DOCUMENTS

| WO | 93-04690 A1 | 3/1993 |
|---|---|---|
| WO | 99/01103 A2 | 1/1999 |
| WO | 03/072124 A1 | 9/2003 |

OTHER PUBLICATIONS

Document No. 139:240332, Caplus retrieved on Jun. 2010.*
Document No. 130:110646, from Caplus retrieved on Jun. 2010.*

D.W. Cushman et al., Design of Potent Competitive Inhibitors of Angiotensin-Converting Enzyme. Carboxyalkanoyl and Mercaptoalkanoyl Amino Acids, Biochemistry, Dec. 13, 1977, pp. 5484-5491, vol. 16, No. 25, American Chemical Society, U.S.A.
Raimondi Stefano et al. "Glutaryl acylase: One reaction enzymes or versatile enantioselective biocatalysts", Advanced Synthesis & Catalysis, 2003, v. 345 (6+7), p. 783-789 (the abstract).
Hans Jurgen Rosenkranz et al. Synthese von Tuboflavin, 4-Athyl-canthin-6-on und Canthin-6-on, Justus Liebigs Annalen Der Chemie, 1966, band 691, pp. 159-164 (link 9, p. 164).
P.A.Galenko-Yaroshevsky et al.Anti-Arrhythmic Activity of Bephol, Suphane, Mexidol and T3-146 Combined with Some Anti-Arrhythmic Agents, Bulletin for Experimental Biology and Medicine, 1998, vol. 125, No. 5, pp. 544-547.
Branko S. Jursic et al. Cyclodextrin assisted enantiomeric recognition of benzo[de]lisoquinoline-1, 3-dione derived amino acids, Tetrahedron, 2005, vol. 61, (4), pp. 919-926, (pp. 924-925, link 2c).

(Continued)

*Primary Examiner* — Shawquia Jackson
(74) *Attorney, Agent, or Firm* — Banner & Witcoff, Ltd.

(57) ABSTRACT

The present invention relates to N-acyl derivatives of amino acids and pharmaceutically acceptable salts thereof

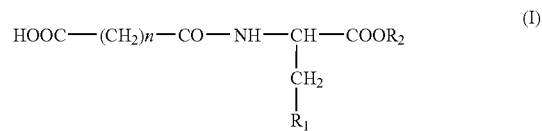

wherein n is 2 or 3; and
$R_1$ represents

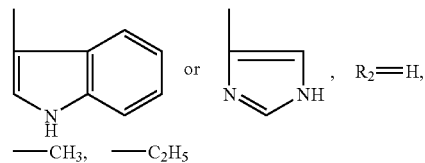

or pharmaceutically acceptable salts thereof, to novel processes for preparing the same, to use thereof as anti-allergic, anti-anaphylactic, anti-inflammatory and hypo-lipidemic agents as well as to a pharmaceutical composition comprising the indicated compounds in an efficient amount and to a method for treating allergic and inflammatory diseases and lipid metabolism disorders: bronchial asthma, allergic rhinitis, pollinoses, seasonal and year-round rhinitis, allergic pneumonitis, atopic dermatitis, psoriasis, urticaria, allergic (including anaphylactic) reactions to insect stings and medicaments, cold allergy, allergic conjunctivitis, atherosclerosis, obesity, ischemic heart and cerebral disease, myocardial infarction and stroke.

17 Claims, 1 Drawing Sheet

(56) References Cited

OTHER PUBLICATIONS

Joseph R. Votano et al. "Inhibition of deoxyhemoglobin S polymerization by biaromatic peptides found to associate with the hemoglobin molecule at a preferred site", Biochemistry, 1985, vol. 24, pp. 1966-1970 (p. 1968, table II).
International Search Report for PCT/RU2006/000311 dated Sep. 20, 2006 (Mailed Oct. 12, 2006).
Sakai et al.; (2006) "Evolution of Enzymatic Activities in the Enolase Superfamily: N-Succinylamino Acid Racemase and a New Pathway for the Irreversible Conversion of D- to L-Amino Acids"; Source: Accession No. 144:483386, retrieved from Caplus 2006 (3 pages total).
Sakai et al.; (2006) "Evolution of Enzymatic Activities in the Enolase Superfamily: N-Succinylamino Acid Racemase and a New Pathway for the Irreversible Conversion of D- to L-Amino Acids"; Source: Biochemistry, vol. 45, No. 14, pp. 4455-4462; Supplementary Materials for Sakai et al., Biochemistry (2006), 45:14, 4455-4462 (26 pages total).

\* cited by examiner

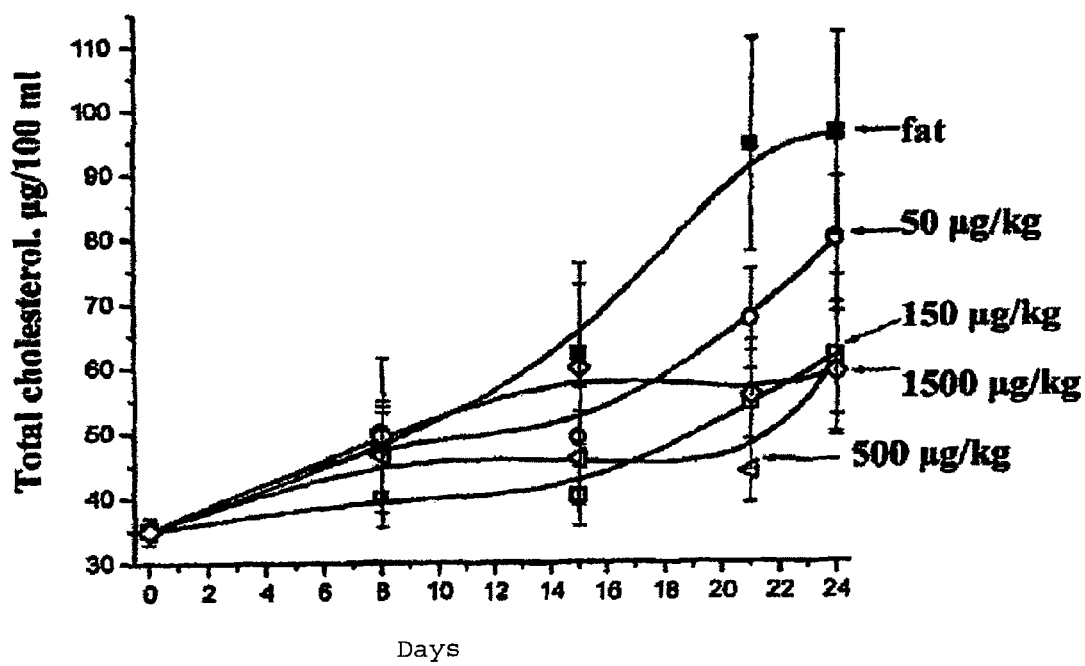

N-ACYLIC AMINOACID DERIVATIVES, METHOD FOR THE PRODUCTION THEREOF, PHARMACOLOGICAL COMPOSITION AND THE USE IN THE FORM ANTI-ALLERGIC, ANTI-INFLAMMATORY AND HYPOLIPIDEMIC AGENTS

The present invention relates to the field of bioorganic chemistry and concerns N-acyl derivatives of amino acids and pharmaceutically acceptable salts thereof, novel processes for synthesis of said compounds as well as pharmaceutical compositions based on them and use thereof in medicine as anti-allergic, anti-inflammatory and hypolipidemic agents.

PRIOR ART

Allergic diseases and lipid metabolism disorders are known to be highly prevalent at the present time because of a poor environmental situation, change in the structure of nutrition and life style of population. Therefore, the problem of developing medicaments for combating these pathologies as well as inflammatory processes accompanying allergy, remains to be actual.

H1-histamine receptor blockers are the most spread group of anti-allergic drugs. At the present time, two generations of anti-histamine drugs are distinguished [Mashkovsky M. D. Lekarstvennye sredstva (Medicaments)/Moscow, the Novaya Volna publishers, 2005, p. 285].

Anti-histamine drugs of the first generation pass through blood-brain barrier and are capable of inducing H1-receptor blockade of the central nervous system cells that causes their adverse sedative effect. High blood concentration of these drugs are required to achieve a pronounced anti-histamine action that requires prescription thereof at high doses. A rather frequent development of tachyphylaxy, effect on the CNS manifested by disordered coordination, dizziness, feeling of flabbiness, lowered ability of concentrating attention are negative characteristics of these drugs. In spite of the aforesaid, anti-histamine agents of the first generation are still used especially in the situations when a very fast treatment effect is needed, for example in anaphylaxis. Dimedrol (diphenhydramine), suprastine (chloropyramine), tavegil (clemastine) and phencarol (chyphenadine) belong to the first generation anti-histamine drugs.

Anti-histamine drugs of the second generation have attained a wide use in allergological practice since they have no adverse effects inherent to the first generation drugs. In particular, the second generation drugs do not pass through the blood-brain barrier, they do not exert sedative and hypnotic effects. These drugs are characterized by a fast and long-lasting anti-histamine action. Claritine (Loratadine), Zirtec (Cetirisine), Kestine (Ebastine) belong to the second generation anti-histamine drugs. However, the conducted clinical trials have revealed side effects of these drugs caused by interaction thereof with other medicaments or by interruption of its metabolism induced by P450 cytochrome. Thus, potentially sedative (Cetirisine, Loratadine) and potentially cardiotoxic (Terphenadine, Asthemisol (Ebastine)) effects have been detected in the second generation anti-histamine agents.

In some cases, for example in bronchial asthma, glucocorticoids exerting a potent anti-allergic action are used. However, use thereof is accompanied by systemic manifestations such as Itsenko-Cushing syndrome, hypertension, hyperkalemia, osteoporosis etc. [Mashkovsky M.D. Lekarstvennye sredstva (Medicaments)/Moscow, 1993, Vol. 1, p. 365].

The pathochemical stage of allergic response development, which to a significant extent is determined by the activation degree of the first order allergy target cells (basophils and mast cells), plays a special role in the development of allergic diseases. Capability of accumulating and releasing biologically active compounds, first of all histamine, under the effect of a stimulus (allergen) is an important feature thereof. In IgE- and/or IgG-mediated response to antigen, just these cells determine degree of manifestation of immediate allergy clinical picture [Parker Ch. V./Mediators: Release and Functions.//In: Immunology. Edited by W. Pole. Moscow, the Mir publishers. 1989. vol. 3. pp. 170-247; Chakravarty N. K.//In: The mast cell: Its role in health and disease, ed. J. Pepys. 1979. p. 38-46].

There is a group of drugs (sodium cromoglycate (cromoglycic acid disodium salt), ketotyphen, oxatomide) useful in bronchial asthma and bronchospastic conditions the action of which is based on the capability of inhibiting mast cell degranulation and hampering release from them of mediator substances promoting the development of bronchial spasms, allergy and inflammation (bradykinin, histamine). Mucosal irritation, headache, laryngeal edema, cough, suffocation may be observed as side effects [Mashkovsky M. D. Lekarstvennye sredstva (Medicaments)/Moscow, the Novaya Volna publishers, 2005, p. 297].

Ischemic heart disease that is the first most frequent cause of lethality of adult population world-wide is known to be the most frequent manifestation of atherosclerosis. Lipid metabolism disorder manifested by elevated blood plasma cholesterol level including low density lipoprotein cholesterol (LDLC) and very low density lipoprotein cholesterol (VLDLC) which are called "atherogenic" lipoproteins with simultaneous decrease in the amount of "anti-atherogenic" lipoproteins is recognized as one of the leading disorders in the instant disease.

Change in plasma lipid content and ratio was shown to reflect modification thereof in membranous structures of parenchymal organs. Composition of cellular membranes, for example macrosomal, is directly depends on the diet given to experimental animals [Wade A., Harred W.//Feder. Proct. 1976, vol. 55. pp. 2475-2479]. Administration of cholesterol to animals induces cholesterol accumulation in cellular membranes decreasing fluidity thereof that in turn, results in functional state modification of enzymes [Buters J. T. M., Zysset T., Reichen J.//Biochem. Pharmacol. 1993. vol. 46. Iss 6. pp. 983-991].

Hypolipidemic agents lowering blood level of cholesterol and triglycerids may be used for treating and preventing diseases associated with lipid metabolism disorders. The latter are characterized by elevated level of triglycerides, total cholesterol (TC), low density and very low density lipoprotein cholesterol (LDLC and VLDLC) and by lowered level of high density lipoprotein cholesterol in such diseases as atherosclerosis, obesity, ischemic heart and cerebral disease, myocardial infarction, stroke and which serve as a risk factor of manifested diabetes and thrombus formation.

Clinical use of so called statines, cholesterol biosynthesis inhibitors, for example zokor (simvastatine) is known. Drugs of the given group at doses 80 mg daily are sufficiently effective mainly with regard to lowering total cholesterol level, but these drugs being poorly available and representing chemical compounds which are xenogenic for the body. Furthermore, use thereof can be accompanied by the side effects such as change in hepatic function with elevated blood transaminase levels and dyspepsia [Mashkovsky M. D. Medicaments./ Meditsina publishers. Moscow. 1993. vol. 1. p. 463].

In view of the foregoing, a search for novel efficient anti-allergic and hypolipidemic agents with alternative mechanisms of action which are capable of manifesting activity at low concentrations and devoid of side effects is actual. With this regard, compounds comprising residues of substances of natural origin are of a special interest as for them, a lower toxicity and a lower occurrence of side effects may be predicted.

In the International application publication WO 99/01103 anti-allergic and hypolipidemic action of N-acyl derivatives of biogenic amines, for example γ-glutamyl histamine and the closest analog thereof glutaryl histamine is disclosed; these compounds are the closest ones by structure and action to the claimed compounds. In the article of Krzhechkovskaya V. V., Zheltukhina G. A., Nebolsin V. E. et al. Study of anti-anaphylactic activity and mechanisms of action of γ-L-glutamyl histamine.//Pathogenez (Pathogenesis). 2003. Vol. 1. No 2, pp. 60-64 γ-glutamyl histamine was shown to possess a frank anti-anaphylactic activity when different animal species and administration rates are used. The results obtained show that in mast cells of animals a significant lowering histamine level and antigen-stimulated secretion thereof occurs under the effect of γ-glutamyl histamine. Decrease in bronchial spasm value more than by 50% as compared to the control was shown in the test of glutaryl histamine effect on manifestation degree of antigen-induced bronchial spasm. The instant effect was manifested in both oral and intratracheal route of administration at a low dose of 50 μg/kg. Glutaryl histamine is capable of lowering manifestations of passive cutaneous anaphylaxis. In WO 99/01103 administration to animals of glutaryl histamine at doses 50 and 500 μg/kg was shown to significantly lower intensity of delayed type hypersensitivity. Furthermore, glutaryl histamine at doses 50 and 500 μg/kg also possessed some anti-cholesterolemic activity lowering total cholesterol by 5 to 7% as compared to animals with atherogenic loading.

Drawback of glutaryl histamine is a comparatively high cost and a poor availability of the starting material for preparation thereof i.e. histamine. Furthermore, the indicated substance is insufficiently effective in the tests mentioned above.

In order to expand arsenal of technical means and to create a more efficient and available anti-allergic, anti-inflammatory and hypolipidemic agent, the inventors have revealed certain specific N-acyl derivatives of amino acids of general formula I disclosed in the International application publication WO 99/01103 but particularly not described, not prepared and not characterized therein except for glutaryl-L-histidine methyl ester (XII).

Thus, the compounds of the instant invention are covered by general formula I of the International application indicated above. However, in the indicated publication neither particular structural formulas of the given compounds nor any physical-chemical characteristics are presented, as well as processes for preparation thereof are not disclosed. The compounds of the instant invention fall under general structural formula of the compounds disclosed in the International application publication WO 03/072124 possessing the inducing cellular differentiation activity. However, in the given publication, a process for synthesis thereof is not disclosed, and any physical-chemical constants are not presented.

One of the compounds, glutaryl histidine, is mentioned only in the form of His C-terminal methyl ester [Glt-His (OMe)(XII)] in the U.S. Pat. No. 3,963,691 as an intermediate used in the synthesis of the peptide Glt-His-Trp-Ser-Tyr-Gly-Leu-Arg-Pro-Gly-poly-Lys. Furthermore, in the International application publication WO 99/01103, synthesis of glutaryl-L-histidine methyl ester (XII) is disclosed and physical-chemical characteristics are presented: data of $^1$H-NMR, mass spectrometry, HPLC.

In the International application publication WO 93/04690, the compound succinyl histidine is mentioned. In this publication, addition of free imidasole or succinyl histidine is indicated to accelerate the reaction between carnosine and dihydroxyacetone. Synthesis of succinyl histidine and physical-chemical constants are not presented.

Structural formula of succinyl pryptophane is mentioned in the US application 2005079515. In the indicated publication, neither synthesis of succinyl tryptophane nor physical-chemical constants are not presented.

In the journal "Byuleten' experimental'noy biologii i meditsiny", 1998, vol. 125, No 5, pp. 544-547, dipotassium salt of N-succinyl-d,l-tryptophane possessing anti-arrhythmic and anti-fibrillation activity is disclosed, which provides anti-ishemic and antihypoxic action and stabilizes hemodynamic parameters in acute myocardial ischemia.

In Justus liebigs annalen der chemie, 1966, Band 691. P. 159-164, racemic succinyl tryptophane is disclosed.

In Tetrahedron, 2005, v. 61, No. 4, P. 919-926, physical-chemical characteristics of succinyl-L-tryptophane and succinyl-D-tryptophane are presented. Any information about biological activity thereof is lacking.

In the article Joseph R. Votano et al. Inhibition of deoxyhemoglobin S polymerization by biaromatic peptides found to associate with the hemoglobin molecule at a preferred site, Biochemistry, 1977, v. 16, No. 25, pp. 5484-5491 succinyl-L-tryptophane is mentioned and capability thereof to bind to deoxyhemoglobin is studied.

In the article Dongmei H., Chao W., Ming Z., Shiqi P. Synthesis and analgesic activity of N,N'-dicarbonyl-tryptamines. Prep. Biochem. & Biotechnol., 2000, V. 30(3), P. 231-240, synthesis of $N^\alpha$-succinyl-L-tryptophane methyl ester (XI) is disclosed originating from tryptophane methyl ester and succinic anhydride in the presence of dimethylamine pyridine with subsequent chromatographic purification of the target product. $N^\alpha$-succinyl-L-tryptophane methyl ester is characterized by physical-chemical data: $^1$H-NMR-, IR-spectroscopy, mass spectrometry, melting point and elemental analysis data.

Gluteryl-L-tryptophane methyl ester (XIII) is mentioned in the article Raimondi S., Monti D., Pagnoni U. M., Riva S. Glutaryl acylases: One-reaction enzymes or versatile enantioselective biocatalysts? Adv. Synth. Catal. 2003. V. 345(6-7). P. 783-789, wherein only typical synthesis technique is presented and only $^1$H-NMR data are presented out of physical-chemical constants. The compound (XIII) was synthesized as a substrate for glutaryl acylase.

Preparation of $N^\alpha$-glutaryl-L-histamine is disclosed in the International application publication WO 99/01103 which process is N-acylation of biogenic amine with glutaric anhydride in the medium of unhydrous N,N-dimethyl formamide. Furthermore, in the publication of Gershkovich A. A., Kibirev V. K.//Chemical synthesis of peptides./Kiev, Naukova Dumka publishers, 1992, p. 360 a process for acylation of amino acids in aqueous-organic, strongly alkaline medium is disclosed.

In the publication of Sorm F., Pravda Z. Proteins and amino acids. X. Synthesis of two peptide analogs.//Chemicke Listy pro Vedu a Prumysl. 1951. V. 45. P. 423-425, a synthesis process of succinyl tyrosine ethyl ester in a mixture of water and ethyl acetate at 1:1 ratio is disclosed originating from tyrosine ethyl ester chlorohydrate and glutaric anhydride in the presence of $NaHCO_3$ for maintaining a weakly alkaline pH.

Free histidine acylation with carboxylic acid anhydrides is not disclosed in the literature.

Object of the instant invention is providing novel effective N-acyl derivatives of amino acids and pharmaceutically acceptable salts thereof possessing anti-allergic, anti-inflammatory and hypolipidemic action at low doses and not showing side effects, pharmaceutical compositions based on them, use thereof as more effective anti-allergic, anti-inflammatory and hypolipidemic agents, as well as novel processes of synthesis of N-acyl derivatives of amino acids.

The inventors have developed a simple and efficient process of synthesis of compounds of general formula I consisting in that glutaric or succinic anhydride in the form of a solid is added to an aqueous solution of an amino acid in the absence of inorganic and organic base with obtaining the target product with a sufficiently high yield of 55 to 60%.

The inventors have developed one more synthesis process of compounds of general formula I including N-acyl derivatives of histidine and tryptophane which process is the reaction in a biphasic system consisting of an aqueous histidine solution or tryptophane salt and an acylating agent solution in a suitable organic solvent in using the acylating agent excess.

SUMMARY OF THE INVENTION

The instant invention relates to novel N-acyl derivatives of amino acids of general formula I:

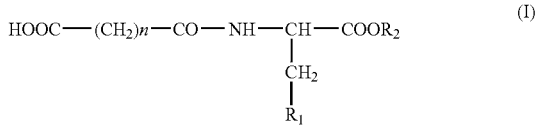

wherein n is 2 or 3; and
$R_1$ represents

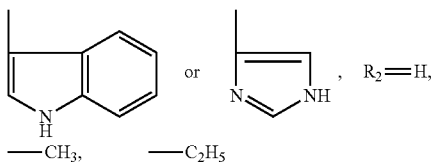, $R_2$=H,

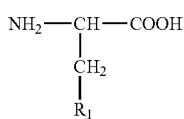

and pharmaceutically acceptable salts thereof possessing anti-allergic, anti-inflammatory and hypolipidemic action.

The instant invention also relates to a process for preparing N-acyl derivatives of amino acids of formula I and salts thereof comprising addition of glutaric or succinic anhydride in the form of a solid to an aqueous amino acid solution of general formula I:

$$NH_2-CH-COOH$$
$$|$$
$$CH_2$$
$$|$$
$$R_1$$

wherein $R_1$ represents

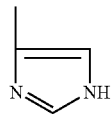

and optionally converting the target product into a salt thereof.

The instant invention further relates to a process for preparing N-acyl derivatives of amino acids and salts thereof which process comprises reacting in a biphasic system of glutaric or succinic anhydride with an aqueous solution of the amino acid of general formula $$NH_2-CH-COOH$$
$$|$$
$$CH_2$$
$$|$$
$$R_1$$

wherein $R_1$ represents

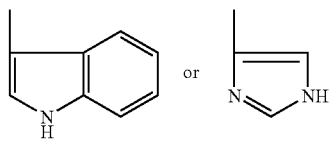

in a water immiscible organic solvent
and optionally converting the target product into a salt thereof.

The instant invention relates also to use of compounds of general formula I and pharmaceutically acceptable salts thereof as anti-allergic, anti-inflammatory and hypolipidemic agents.

Further, the instant invention relates to pharmaceutical compositions and an agent possessing anti-allergic, anti-anaphylactic, anti-inflammatory and hypolipidemic action comprising an effective amount of the compound of formula I or a pharmaceutically acceptable salt thereof as well as if needed a pharmaceutically acceptable carrier.

One more object of the invention is a method for treating allergic diseases including bronchial asthma, allergic rhinitis, pollinoses, seasonal rhinitis, round-year rhinitis, atopic dermatitis, psoriasis, urticaria, allergic (including anaphylactic (reactions to insect stings and medicaments, cold allergy, allergic conjunctivitis, chronic obstructive pulmonary diseases, namely chronic obstructive bronchitis, emphysema, obliterating bronchitis, mucoviscedosis, as well as diseases related to lipid metabolism disorders: atherosclerosis, obesity, ischemic heart and cerebral disease, myocardial infarction, stroke, which method comprises administering to a subject an effective amount of the compound of general formula I or a pharmaceutically acceptable salt thereof.

DETAILED DISCLOSURE OF THE INVENTION

Preferable compounds of general formula I are presented in Table 1.

TABLE 1

| Compound | Compound number | R₁ | R₂ | n |
|---|---|---|---|---|
| $N^\alpha$-succinyl-L-tryptophane | II | (Ind) | H | 2 |
| $N^\alpha$-glutaryl-L-tryptophane | III | Ind | H | 3 |
| $N^\alpha$-glutaryl-L-histidine | IV | (Im) | H | 3 |
| $N^\alpha$-succinyl-L-histidine | V | Im | H | 2 |
| $N^\alpha$-succinyl-L-histidine methyl ester | VI | Im | —CH₃ | 2 |
| $N^\alpha$-succinyl-L-histidine ethyl ester | VII | Im | —C₂H₅ | 2 |
| $N^\alpha$-succinyl-L-tryptophane ethyl ester | VIII | Ind | —C₂H₅ | 2 |
| $N^\alpha$-glutaryl-L-tryptophane ethyl ester | IX | Ind | —C₂H₅ | 3 |
| $N^\alpha$-glutaryl-L-histidine ethyl ester | X | Im | —C₂H₅ | 3 |
| $N^\alpha$-succinyl-L-tryptophane methyl ester | XI | Ind | —CH₃ | 2 |
| $N^\alpha$-glutaryl-L-histidine methyl ester | XII | Im | —CH₃ | 3 |
| $N^\alpha$-glutaryl-L-tryptophane methyl ester | XIII | Ind | —CH₃ | 3 |

Synthesis of compounds of general formula I can be accomplished by two processes. The first process consists in a gradual adding to an aqueous solution of an amino acid of general formula

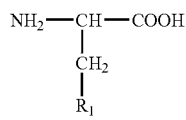

wherein R₁ represents

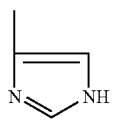

glutaric or succinic anhydride in the form of a solid with subsequent isolation of the target product using ion exchange chromatography, preferably by passing reaction mixture through a column with cationite and subsequent crystallization from aqueous solution. The crystals of the target product obtained are washed with a suitable solvent, preferably methanol. The main advantage of the claimed process consists in the absence of alkali in the amino acid aqueous solution that prevents from inactivation of dicarboxylic acid anhydride resulting from hydrolysis. Furthermore, imidazol residue in the amino acid molecule can effect acidic-basic autocatalysis of acylation reaction of the amino group of amino acid. Rather high yields (55-60%) in using the claimed process are achieved in particular due to a gradual adding dicsarboxylic acid anhydride taken in the excess, and to vigorous stirring reaction mass.

Compounds of general formula I can be also prepared using an alternative process in a biphasic system which process comprises adding glutaric or succinic anhydride in a water immiscible solvent to an aqueous solution of the amino acid of general formula:

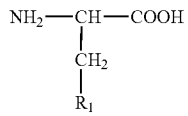

wherein R₁ represents

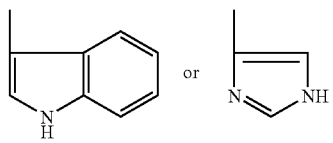

The instant process allows to use the excess of an acylating agent, achieve the complete acylation of α-amino group of the amino acid and yield of the target product of about 70%. In order to maintain required pH, instead of an inorganic alkali, the organic base pyridine is used which does not hydrolyze anhydride and in addition is known to be catalyst of acylation.

Using pyridine allows for avoiding contamination of the final product by inorganic salts which together with the reaction product remain in aqueous layer. The used approaches allow for simplifying separation of the target product from non-reacted anhydride and respective amino acid and isolating the target product by a simple crystallization.

Preferable water immiscible organic solvents are butanol, ethylacetate and chloroform.

Preferable solvents useful for crystallizing the target product are water-alcohol mixtures, in particular, water-ethanol.

N-acyl derivatives of amino acid esters of invention (VI-XIII) can be prepared by the action of respective internal anhydrides of dicarboxylic acids on amino-free histidine or tryptophane esters in an organic or water-organic medium. Preferable is preparing the compounds VI-XIII in a biphasic system using water immiscible organic solvents butanol, ethylacetate and chloroform.

Compounds of general formula I can also be prepared in the form of pharmaceutically acceptable salts by reacting for example with sodium hydroxide, potassium hydroxide, magnesium carbonate, lithium hydroxide, calcium carbonate using routine processes widely disclosed in the literature.

Compounds of general formula I have anti-allergic, anti-inflammatory and hypolipidemic activity and they can be used for treating allergic, anaphylactic diseases including those accompanied by inflammation, as well as lipid metabolism disorders.

In particular, compounds of the present invention may be used for treating the following allergic diseases: bronchial asthma, allergic rhinitis, pollinoses, seasonal rhinitis, round-year rhinitis, atopic dermatitis, psoriasis, urticaria, allergic (including anaphylactic) reactions to insect stings and medicaments, cold allergy, allergic conjunctivitis, chronic obstructive pulmonary diseases, namely chronic obstructive bronchitis, emphysema, obliterating bronchitis, mucoviscedosis, as well as diseases related to lipid metabolism disorders such as: atherosclerosis, obesity, ischemic heart and cerebral disease, myocardial infarction and stroke.

Compounds of the present invention are administered in an effective amount which provides for a desirable therapeutic result.

For treating allergic diseases including bronchial asthma, allergic rhinitis, pollinoses, seasonal rhinitis, round-year rhinitis, atopic dermatitis, psoriasis, urticaria, allergic (including anaphylactic) reactions to insect stings and medicaments, cold allergy, allergic conjunctivitis, chronic obstructive pulmonary diseases, namely chronic obstructive bronchitis, emphysema, obliterating bronchitis, mucoviscedosis, as well as diseases related to lipid metabolism disorders such as: atherosclerosis, obesity, ischemic heart and cerebral disease, myocardial infarction and stroke, compounds of general formula I may be administered perorally, topically, parenterally, nasally, by inhalation or rectally in unit dosage forms comprising non-toxic pharmaceutically acceptable carriers. As used in the instant disclosure, the term "parenteral administration" means subcutaneous, intravenous, intramuscular or intraperitoneal injections or infusions.

Compounds of the present invention can be administered to a patient at doses from 0.01 to 10 mg/kg body weight daily, preferably at doses from 0.05 to 5 mg/kg once or more times daily.

At the same time, it should be noted that a particular dose for each particular patient will depend on many factors including activity of a given compound used, age, body weight, sex, general health condition and nutrition regimen of the patient, time and route of administering a medicament, elimination rate thereof from the body, a particular combination of medicaments used as well as on severity of disease to be treated in the given individual.

Pharmaceutical composition of the instant invention comprise the compound of general formula I in an amount effective to achieve a desired result and can be administered in unit dosage forms (for example in a solid, semisolid or liquid forms) comprising compounds of the instant invention as an active ingredient in admixture with a carrier or excipient suitable for intramuscular, intravenous, peroral, sublingual, inhalation, intranasal and intrathecal administration. Active ingredient can be included into a composition together with conventionally used non-toxic pharmaceutically acceptable carriers suitable for manufacturing solutions, tablets, pellets, capsules, dragee, suppositories, emulsions, suspensions, ointments, gels and any other dosage forms.

As excipients, different substances such as saccharides for example glucose, lactose or sucrose mannitol or sorbitol, cellulose derivatives and/or calcium phosphate for example tricalcium phosphate or acidic calcium phosphate may be used, and as a binding component, such materials as starch paste, for example corn, wheat, rise, potato starch, gelatine, tragacant, methylcellulose, hydroxypropyl methylcellulose, sodium carboxymethylcellulose and/or polyvinylpyrrolidone. If needed, disintegrants such as the above mentioned starches and carboxymethyl starch, cross-linked polyvinylpyrrolidone, agar or alginic acid or a salt thereof such as sodium alginate can be used.

Optional additives such as agents controlling fluidity and lubricants such as silica, talc, stearic acid and salts thereof such as magnesium stearate or calcium stearate and/or propyleneglycol can be used.

A core is usually coated by a layer which is resistant to the action of gastric juice. For this, concentrated solutions of saccharides can be used which solutions may optionally comprise gum Arabic, talc, polyvinyl pyrrolidone, polyethylene glycol and/or titanium dioxide, and suitable organic solvents or mixtures thereof.

As additives, stabilizers, thickeners, colorants and flavours can be also used.

As an ointment base, carbohydrate ointment bases such as white and yellow vaseline (Vaselinum album, Vaselinum flavum), Vaseline oil (Oleum Vaselini), white and liquid ointment (Unguentum album, Unguentum flavum) can be used, and as additives for imparting a more compact consistence, hard paraffin and wax, absorbtive ointment bases such as hydrophilic vaseline (Vaselinum hydrophylicum), lanoline (Lanolinum), coldcream (Unguentum leniens); ointment bases washable with water such as hydrophilic ointment (Unguentum hydrophylum); water soluble ointment bases, such as polyethylene glycol ointment (Unguentum Glycolis Polyaethyleni), bentonite bases and others can be used.

As a base for gels, methylcellulose, carboxymethylcellulose sodium salt, oxypropylcellulose, polyethylene glycol or polyethylene oxide and carbopol can be used.

As a base for suppositories, water insoluble bases such as cocoa butter; water soluble or water miscible bases such as gelatin-glycerol or polyethylene oxide and combined (soap-glycerol) can be used.

In preparing a unit dosage form, an amount of an active ingredient used in a combination with a carrier may vary depending on a recipient subjected to therapy, a particular administration route of a medicament.

Thus, in using compounds of the instant invention in the form of solutions for injections, content of an active ingredient therein is 0.01 to 5%. As diluents, 0.9% sodium chloride solution, distilled water, novocaine solution for injections, Ringer solution, glucose solution and specific additives for dissolution can be used. In administering compounds of the instant invention into the body in the form of tablets and suppositories, their amount is from 5.0 to 500.0 mg per an unit dosage form.

Dosage forms of the instant invention are manufactures according to the standard techniques such as for example processes of mixing, granulation, forming dragee, dissolution and freeze-drying.

It should be noted that compounds of the instant invention show biological activity at doses that are by two-three folds lower than those of the known drugs used for comparison, in a practically similar efficacy, and for them, no adverse side effect have been detected, and contraindication for their use have not been found. At the same time, in examining toxicity of compounds according to the instant invention at a dose 3,000 mg/kg orally, death of experimental animals has not been recorded.

Detailed description of the compounds according to the present invention, preparation thereof and the study of pharmacological activity is presented in the following examples intended for illustration of preferable embodiments of the invention and not limiting the scope thereof.

Synthesis Examples of N-Acyl Derivatives of General Formula I

Individuality of the prepared compounds has been checked using TLC method on the plates "Kieselgel 60 $F_{254}$" "Merck" (Germany) in the systems: methanol (1), chloroform-methanol-ammonia (4:3:1) (2).

Chromatograms were developed by a chlorotolidine reagent, ninhydrine, iodine by luminescence in UV light.

Optic rotation angles were measured on the polarometer "Perkin Elmer 341" (Sweden).

$^1$H-NMR was recorded on the apparatus "AMX-400 Bruker" (Germany).

Melting point was determined on the apparatus "Boetius" (Germany).

Analytical HPLC was carried out on the apparatus "System Gold" ("Beckman", USA), elution rate 0.25 ml/min; detection at 214 nm under the following conditions: column Ultrasphere ODS "Beckman", 2×250 mm, 5 μm, elution with 0.1% TFA, elution rate 0.25 ml/min (1); eluting rate 1 ml/min, detection at 220 nm; column Luna-5 "Phenomenex", $C_{18}$, 250×4.6 mm, elution 25% acetonitryl in 0.05 M phosphate buffer (pH 3.0) (2).

Example 1

$N^\alpha$-glutaryl-L-histidine (IV)

Technique A

To solution of 103.4 g (0.67 mmol) histidine in 400 ml water 83.7 g (0.73 mol) glutaric anhydride were added. Suspension was stirred for 1 hour, the formed solution was boiled down to the volume 150 ml, left in a refrigerator for 16 hours. Precipitate was filtered off, washed with 150 ml ethanol and dried. Purification was carried out by ion exchange chromatography on the resin Purolight in $H^+$ form eluting with water. Fractions comprising the target product were combined, boiled down until precipitation begun and left for 16 hours at 4° C. Precipitate was filtered off, washed with 200 ml methanol and dried to a constant weight. Yield 98.8 g (55%). $R_f$ 0.55 (1), 0.37 (2). $T_{m.p.}$=222-224° C. $[\alpha]_D^{20}$+15.95° (C 0.53, water). $[M+H]^+$ 270.1. $^1$H NMR spectrum ($D_2O$), δ, m.d.: 1.60-1.80 (m, 2H, β-$CH_2$-Glt), 2.10-2.25 (m, 4H, α,γ-$CH_2$-Glt), 2.90-3.25 (m, 2H, β-$CH_2$-His), 4.40-4.50 (m, 1H, α-CH-His), 7.15 (s, 1H, CH-4-Im), 8.50 (s, 1H, CH-2-Im). Found, %: C, 49.18; H, 5.91; N, 15.42. $C_{11}H_{15}N_3O_5$. Calculated, %: C, 49.07; H, 5.62; N, 15.61.

Technique B

To suspension of 0.3 g (1.93 mmol) histidine in 5 ml water under vigorous stirring 0.44 g (3.86 mmol) glutaric anhydride dissolved in 2.5 ml ethylacetate is added. The suspension was stirred for 2 hours, pH was adjusted to 7 with pyridine and stirred for another 1 hour. Ethylacetate and aqueous layers were separated. Aqueous layer was twice washed with ester, ester layer was discharged. Water was removed in vacuo, precipitate was dissolved in a minimum amount of water and ethanol was added prior to beginning sedimentation of a white precipitate, left at +4° C. for 20 hours. Precipitate was filtered off, dried in vacuo. Yield 0.36 g (70%). $R_f$ 0.56 (1), 0.35 (2). $T_{m.p.}$=219-221° C. $[\alpha]_D^{20}$=+15.74° (C 0.56, water). $[M+H]^+$ 270.1.

$^1$H-NMR spectrum ($D_2O$), δ, m.d.: 1.40-1.55 (m, 2H, β-$CH_2$-Glt), 1.90-2.0 (m, 4H, α, γ-$CH_2$-Glt), 2.7-3.0 (m, 2H, β-$CH_2$-His), 4.20-4.30 (m, 1H, α-CH-His), 6.95 (s, 1H, 4-CH-Im), 8.30 (s, 1H, 2-CH-Im). HPLC under the conditions: (1)—individual peak, retention time 14.55 min.

Found, %: C, 49.07; H, 5.65; N, 15.65. $C_{11}H_{15}N_3O_5$. Calculated, %: C, 49.07; H, 5.62; N, 15.61.

Example 2

$N^\alpha$-succinyl-L-histidine (V)

Synthesis was carried out in accordance with the technique A presented for compound IV.

Yield 0.08 g (57%).

$R_f$ 0.44 (1), 0.25 (2).

$T_{m.p.}$=179-181° C.

$[\alpha]_D^{20}$=+30.71° (C 0.56, water).

$[M]^+$ 255.2.

$^1$H-NMR spectrum ($D_2O$), δ, m.d.: 2.15-2.30 (m, 4H, $(CH_2)_2$-Suc), 2.75-2.95 (m, 2H, β-$CH_2$-His), 4.25 (br.s, 1H, α-CH-His), 6.95 (s, 1H, 4-CH-Jm), 8.25 (s, 1H, 2-CH-Jm).

Found, %: C, 47.09; H, 5.04; N, 16.40. $C_{10}H_{13}N_3O_5$. Calculated, %: C, 47.06; H, 5.13; N, 16.46

Synthesis was carried out according to the technique B carried out for compound IV.

Yield 0.101 r (67%).

$R_f$ 0.45 (1), 0.27 (2).

$T_{m.p.}$=178-180° C.

$[\alpha]_D^{20}$=+30.8° (C 0.57, water).

HPLC under the conditions (1)—individual peak, retention time 7.54 ммин н.

Found %: C, 47.15; H, 5.2; N, 16.50. $C_{10}H_{13}N_3O_5$. Calculated %: C, 47.06; H, 5.13; N, 16.46.

Example 3

$N^\alpha$-Glutaryl tryptophane (III)

To suspension of 1.0 g (4.9 mmol) tryptophane in 7 ml water 1 N NaOH solution (4.9 mmol) was added drop-wise. To the prepared solution, solution of 0.56 g (4.9 mmol) glutaric aldehyde in 3 ml ethylacetate were added. Reaction mixture was stirred for 3 hours at room temperature under argon in darkness and left for 16 hours at +4° C. Solvent was removed from the reaction mixture in vacuo. The oily residue obtained was dissolved in 30 ml water while stirring, cooled down to 0° C., and 1 N HCl was added to adjust pH to 4. The product was extracted with ethylacetate (3×25 ml). The combined ethylacetate extract was cooled down to 0° C., washed with water (4×25 ml) to adjust pH to 7, washed with 5% HCl (5 ml) and washed with water (4×25 ml) adjust pH to 7.0, dried over anhydrous $Na_2SO_4$ for 1 hour. Residue of $Na_2SO_4$ was filtered off, washed with ethylacetate, the solvent was removed in vacuo. Grayish solid precipitate was obtained which was dried in vacuo.

Yield 1.0 g (70%).
$R_f$ 0.54 (1).
$T_{m.p.}$=150-152° C.
$[\alpha]_D^{20}$=+8.20° (C 0.5, methanol).
$^1$H-NMR spectrum (CD$_3$OD), δ, m.d.: 1.75-1.84 (m, 2H, β-CH$_2$-Glt), 2.15-2.30 (m, 4H, α,γ-CH$_2$-Glt), 3.30-3.40 (m, 2H, β-CH$_2$-Trp), 3.80-3.90 (m, 1H, α-CH-Trp), 6.97 (t, J=7 Hz, 1H, CH-6-Ind), 7.06 (t, J=7 Hz, 1H, CH-7-Ind), 7.15 (d, J=7 Hz, 1H, CH-2-Ind), 7.33 (d, J=7 Hz, 1H, CH-5-Ind), 7.55 (d, J=7 Hz, 1H, CH-8-Ind).

HPLC under the conditions: (2)—individual peal, retention time 6.77 minutes.

Found, %: C, 60.07; H, 5.65; N, 8.75. $C_{16}H_{18}N_2O_5$. Calculated, %: C, 60.37; H, 5.7; N, 8.8.

Example 4

N$^\alpha$-Succinyl-L-tryptophane (II)

Synthesis was carried out in accordance with the technique presented for the compound III.

Yield 100.5 mg (67%).
$R_f$ 0.63 (1).
$[\alpha]_D^{20}$=+21.05° (C 0.6, water).
$^1$H-NMR spectrum (DMSO-d$_6$), δ, m.d.: 2.33-2.41 (d, 4H, α,β-CH$_2$-Suc), 2.93-3.01 (d, 1H, β-CH$_2$-Trp), 3.10-3.16 (m, 1H, β-CH$_2$-Trp), 4.39-4.47 (m, 1H, α-CH-Trp), 6.93-7.06 (m, 2H, CH-6,7-Ind), 7.11 (d, J=2.2 Hz, 1H, CH-2-Ind), 7.30-7.32 (m, 1H, CH-5-Ind), 7.44-7.47 (m, 1H, CH-8-Ind). [M]$^+$ 304.3.

HPLC under the conditions: (2)—individual peal, retention time 6.35 minutes.

Found, %: C, 59.07; H, 5.65; N, 9.35. $C_{15}H_{16}N_2O_5$. Calculated, %: C, 59.21; H, 5.3; N, 9.21.

Example 5

N$^\alpha$-glutaryl-L-histidine monosodium salt (IV)

To a solution of 1.0 g (3.7 mmol) of N$^\alpha$-glutaryl-L-histidine in 15 ml water, a solution of 0.15 g (3.7 mmol) NaOH in 20 ml water was added while stirring and cooling down to +5° C. The solution was stirred for 30 min, the solvent was removed in vacuo. To an oily residue, benzene was added in portions, the solvent was removed in vacuo. A solid residue was dried over granulated alkali.

Yield 1.07 g (99.7%).
$T_{m.p.}$=208-210° C.
$[\alpha]_D^{20}$=+16.27° (C 0.58, water).
Found, %: C, 45.25; H, 5.51; N, 14.52. $C_{11}H_{15}N_3O_5Na$. Calculated, %: C, 45.21; H, 5.17; N, 14.38.

Example 6

N$^\alpha$-succinyl-L-histidine monosodium salt (V)

Synthesis was carried out in accordance with the technique presented for N$^\alpha$-glutaryl-L-histidine monosodium salt (IV) (Example 5).
Yield 1.06 g (97.0%).
$[\alpha]D^{20}$=+40.21° (C 0.48, water).
Found, %: C, 43.25; H, 4.51; N, 15.52. $C_{10}H_{13}N_3O_5Na$. Calculated, %: C, 43.17; H, 4.71; N, 15.10.

Example 7

N$^\alpha$-succinyl-L-tryptophane monosodium salt (II)

Synthesis was carried out in accordance with the technique presented for N$^\alpha$-glutaryl-L-histidine monosodium salt (IV) (Example 5).
Yield 0.21 g (98.0%).
$T_{m.p.}$=147-150° C.
$[\alpha]_D^{20}$=+22.02° (C 0.39, water).
Found, %: C, 55.25; H, 4.51; N, 8.32. $C_{15}H_{16}N_2O_5Na$. Calculated, %: C, 55.05; H, 4.93; N, 8.56.
HPLC under the conditions: (2)—individual peal, retention time 6.56 minutes.

Example 8

N$^\alpha$-glutaryl-L-tryptophane monosodium salt (III)

Synthesis was carried out in accordance with the technique presented for N$^\alpha$-glutaryl-L-histidine monosodium salt (IV) (Example 5).
Yield 0.11 g (99.0%).
$T_{m.p.}$=128-130° C.
$[\alpha]_D^{20}$=+22.06° (C 0.34, methanol).
Found, %: C, 56.15; H, 5.21; N, 8.22. $C_{16}H_{18}N_2O_5Na$. Calculated, %: C, 56.30; H, 5.32; N, 8.21.
HPLC under the conditions: (2)—individual peal, retention time 6.96 minutes.

Example 9

N$^\alpha$-glutaryl-L-histidine monosodium salt (IV)

To a solution of 1.0 g (3.7 mmol) N$^\alpha$-glutaryl-L-histidine in 15 ml water a solution of 0.3 g (7.44 mmol) NaOH in 15 ml water was added while stirring and cooling down to +5° C. The solution was stirred for 30 min, the solvent was removed in vacuo. To an oily residue, benzene was added in portions, the solvent was removed in vacuo. A solid residue was dried over granulated alkali.
Yield 1.15 g (99.0%).
$[\alpha]_D^{20}$=+11.92° (C 0.57, water).
Found, %: C, 41.25; H, 4.51; N, 13.52. $C_{11}H_{15}N_3O_5Na_2$. Calculated, %: C, 41.91; H, 4.80; N, 13.3.

Example 10

N$^\alpha$-succinyl-L-histidine disodium salt (V)

Synthesis was carried out in accordance with the technique presented for N$^\alpha$-glutaryl-L-histidine disodium salt (IV) (Example 9).
Yield 1.16 g (99.0%).
$T_{m.p.}$=124-128° C.
$[\alpha]_D^{20}$=+20.06° (C 0.67, water).
Found, %: C, 39.55; H, 4.31; N, 13.52. $C_{10}H_{13}N_3O_5Na_2$. Calculated, %: C, 39.88; H, 4.35; N, 13.95.

Example 11

N$^\alpha$-succinyl-L-tryptophane disodium salt (H)

Synthesis was carried out in accordance with the technique presented for N$^\alpha$-glutaryl-L-histidine disodium salt (IV) (Example 9).

Yield 0.56 g (97.7%).
Found, %: C, 51.35; H, 4.31; N, 8.22. $C_{15}H_{16}N_2O_5Na_2$. Calculated, %: C, 51.43; H, 4.60; N, 8.0.

Example 12

N$^\alpha$-glutaryl-L-tryptophane disodium salt (III)

Synthesis was carried out in accordance with the technique presented for N$^\alpha$-glutaryl-L-histidine disodium salt (IV) (Example 9).
Yield 0.56 g (98.5%).
Found, %: C, 52.55; H, 4.71; N, 7.52. $C_{16}H_{18}N_2O_5Na_2$. Calculated, %: C, 52.75; H, 4.98; N, 7.69.

Example 13

N$^\alpha$-succinyl-L-histidine methyl ester

To a solution of 1.0 g (4.13 mmol) histidine methyl ester in 5 ml of N,N-dimethylformamide 5 ml water and a solution of 0.41 g (4.13 mmol) succinic anhydrife in 2.5 ml ethylacetate were added in vigorous stirring. The mixture was stirred for 2 hours at room temperature. Ethylacetate and water layer were separated. Water layer was washed twice with ester, ester layer was discarded. Water was removed in vacuo, a residue was triturated with 10 ml hexane. A residue was filtered off and dried in vacuo.
Yield 0.70 g (67%).
$R_f$ 0.38 (1).
$T_{m.p.}$=171-173° C.
$^1$H-NMR spectrum (DMSO-d$_6$), δ, m.d.: 2.26-2.37 (m, 4H, α,β-CH$_2$-Suc), 2.70 (s, 3H, —O—CH$_3$), 2.76-2.87 (m, 2H, β-CH$_2$-His), 4.33-4.45 (m, 1H, α-CH$_2$-His), 6.78 (s, 1H, 4-CH-Im), 7.93 (s, 1H, 2-CH-Im), 8.25 (d, J=7 Hz, NH-amide.). $[\alpha]_D^{20}$=+11.92° (C 0.57, water).

According to similar typical techniques, the novel compounds of general formula I presented in Table 2 were also prepared.

TABLE 2

Structure and characteristics of compounds of general formula I

| Compound No | R$_1$ | R$_2$ | n | Physical-chemical characteristics |
|---|---|---|---|---|
| VII | Im | —C$_2$H$_5$ | 2 | $^1$H-NMR spectrum (DMSO-d$_6$), δ, m,d,: 1.12 (t, J = 6.7 Hz, 3 H, —CH$_3$), 2.15-2.27 (m, 4 H, α,β-CH$_2$-Suc), 2.37 (s, 5 H, —O—C$_2$H$_5$), 2.70-2.85 (m, 2 H, β-CH$_2$-His), 3.57 (q, J = 6.7 Hz, 2 H, —O—CH$_2$—), 4.27 (br.s, 1 H, α-CH-His), 6.97 (s, 1 H, 4-CH-Jm), 8.35 (s, 1 H, 2-CH-Jm). [M]$^+$ 283.3 |
| VIII | 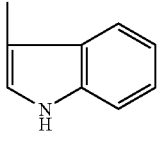 (Ind) | —C$_2$H$_5$ | 2 | $^1$H-NMR spectrum (DMSO-d$_6$), δ, m.d.: 1.11 (t, J = 6.7 Hz, 3 H, —CH$_3$), 2.35-2.45 (m, 4 H, α,β-CH$_2$-Suc), 2.93-3.01 (m, 1 H, β-CH$_2$-Trp), 3.10-3.16 (m, 1 H, β-CH$_2$-Trp), 3.55 (q, J = 6.7 Hz, 2 H, —O—CH$_2$—), 4.39-4.47 (m, 1 H, α-CH-Trp), 6.93-7.06 (m, 2 H, CH-6,7-Ind), 7.11 (d, J = 2.2 Hz, 1 H, CH-2-Ind), 7.30-7.32 (m, 1 H, CH-5-Ind), 7.44-7.47 (m, 1 H, CH-8-Ind). [M]$^+$ 304.3 [M]$^+$ 332.4. Found, %: C 61.51; H 6.10; N 8.52. $C_{11}H_{15}N_3O_4$. Calculated, %: C 61.44; H 6.07; N 8.43 |
| IX | Ind | —C$_2$H$_5$ | 3 | $^1$H-NMR spectrum (DMSO-d$_6$), δ, m.d.: 1.12 (t, J = 6.7 Hz, 3 H, —CH$_3$), 1.78-1.85 (m, 2 H, β-CH$_2$-Glt), 2.15-2.30 (m, 4 H, α,γ-CH$_2$-Glt), 3.27-3.35 (m, 2 H, β-CH$_2$-Trp), 3.57 (q, J = 6.7 Hz, 2 H, —O—CH$_2$—), 3.81-3.93 (m, 1 H, α-CH-Trp), 6.95 (t, J = 7 Hz, 1 H, CH-6-Ind), 7.07 (t, J = 7 Hz, 1 H, CH-7-Ind), 7.17 (d, J = 7 Hz, 1 H, CH-2-Ind), 7.35 (d, J = 7 Hz, 1 H, CH-5-Ind), 7.57 (d, J = 7 Hz, 1 H, CH-8-Ind). [M]$^+$ 346.4 |
| X | Im | —C$_2$H$_5$ | 3 | $^1$H- NMR spectrum (DMSO-d$_6$), δ, m.d.: 1.11 (t, J = 6.7 Hz, 3 H, —CH$_3$), 1.67-1.83 (m, 2 H, β-CH$_2$-Glt), 2.10-2.25 (m, 4 H, α,γ-CH$_2$-Glt), 2.90-3.25 (m, 2 H, β-CH$_2$-His), 3.57 (q, J = 6.7 Hz, 2 H, —O—CH$_2$—), 4.40-4.50 (m, 1 H, α-CH-His), 7.15 (s, 1 H, CH-4-Im), 8.55 (s, 1 H, CH-2-Im). Found, %: C 49.18; H 5.91; N 15.42. $C_{11}H_{15}N_3O_5$. Calculated, %: C 49.07; H 5.62; N 15.61, [M]$^+$ 297.3 |

Tests for Biological Activity

Example 14

Effect of Compounds of General Formula I on Immediate Type Allergic Reactions (In Vitro Test of Ovalbumin (OA)-Induced Blood Basophil Degranulation of Immunized Guinea Pig)

Leukocytes from guinea pig blood were isolated according to the Freemel's method [Immunologicheskiye Metody under edition of G. Frimel/Moscow, "Meditsina" publishers, 1987, p. 222 in the inventor's modification].

Guinea pigs of both sexes weighing from 600 to 800 g were used to conduct the test. The animals were once immunized with a mixture of 10 µg ovalbumin and 100 mg aluminum hydroxide per one animal according to Andersson [Anderson P. Antigen-induced bronchial anaphylaxis in actively sensitized guinea-pigs.//Allergy. 1980. Vol. 35. P. 63-71].

Under ester anesthesia, 15 ml blood were drawn from guinea pig heart. Double precipitation of cells using EDTA and a citrate-containing precipitating liquid was used to isolate basophils in the leukocyte suspension.

Blood was mixed with 5% $EDTA.Na_2$ $2H_2O$ ("Sigma") solution at 9:1 ratio and in 30 minutes it was subjected to mild centrifugation (for 12 minutes at 80 g). Supernatant was collected and centrifuged for 15 minutes at 500 g.

To the remaining cells, a citrate-containing precipitating liquid (3) was added at proportion 3:10 (it was thermostated at 37° C. for 30 minutes). A supernatant fraction enriched by leukocytes was centrifuged for 7 minutes at 100 g. To leukocyte precipitate, 0.85% NaCl solution was added and cellular concentration was brought to $30 \times 10^3/\mu l$.

Protocol of the In Vitro Basophil Degranulation Test

[Spravochnil po klinicheskim laboratornym metodam issledovaniya (A reference book on clinical-laboratory examination methods)/Edited by E. A. Cost/Moscow, "Meditsina" publishers, 1975, p. 130].

For the test, a centrifuge tube (3 tubes per each sample) was filled with 300 µl cellular suspension, then salt solution of a tested compound (or a salt solution in the control of spontaneous and maximum degranulation) was added and pre-incubated at 37° C. for 15 minutes, then into each tube 300 µl 1% OA solution was added (in the control of spontaneous degranulation a salt solution in the same amount was added) and once more pre-incubated at 37° C. for 10 minutes. Functional leukocyte concentration was $10^4/\mu l$. Samples (100 µl) were taken off from each tube into separate tubes to assess a complete basophil degranulation, and to the remained cells, a cooled salt solution was added (5 ml into each tube) to arrest degranulation reaction, then the tubes were centrifuged for 7 min at 100 g, and from precipitate, preparations for microscopy were prepared. The preparations were fixed and stained according to the method of Seder et al. [Seder R. A. et al. Mouse splenic and bone marrow cell populations that express high—affinity Fcε receptors and produce interleukin-4 are highly enriched in basophils.//Proc. Natl. Acad. USA, 1991, V. 88, P. 2835-2839].

In order to detect a specific basophil granulation, the dye 0.5% alcyanic blue (pH 1.0) was used, nuclei were additionally stained with safranin (0.1% solution in 1% acetic acid). The preparations were used to assess a total degranulation inhibition.

A total degranulation inhibition (DI) (%) was calculated according to the formula:

$$DI = \frac{(\max - \text{experimental})}{(\max - \text{spontaneous})} \times 100(\%),$$

wherein max—% of degranulated basophils at the maximum degranulation (OA)

spontaneous—% of degranulated basophils in spontaneous degranulation (control)

experimental—% of degranulated basophils following exposure to the tested compound.

Assessment of a Complete Basophil Degranulation

Samples selected following basophil degranulation test (100 µl each) were poured into tubes with the dye (0.5% alcyane blue, pH 1.0) at ratio 1:1. Staining was carried out at room temperature for not less than 50 min. Stained basophils were calculated using the Fooks-Rosenthal chamber. Inhibition of a complete basophil degranulation (ICD) was calculated according to the formula:

$ICD(\%)=1-[(Mm(c)-Mm(\text{exper.})]/[Mm(c)-Mm(OA)] \times 100$, wherein

M m (c)—mean (by three samples) basophil number in the spontaneous basophil degranulation test;

M±m (OA)—mean (by three samples) basophil number in the maximum antigen-induced basophil degranulation test;

M±m (exper.)—mean (by three samples) basophil number in the basophil degranulation test following incubation with the tested compound.

TABLE 3

In vitro inhibition of OA-induced basophil degranulation of guinea pig blood as effected by compounds of general formula I

| Order No of test | Groups | Complete degranulation inhibition (CDI), (%) | Number of completely degranulated basophils, (%) |
|---|---|---|---|
| 1. | Control 1 (spontaneous degranulation) | 100 | 0 |
| 2. | Ovalbumin 1% (max degranulation) | 0 | 35.2 ± 0.8 |
| 3. | Compound IV ($10^{-3}$ M) | 99.2 ± 11.2 | 2.6 ± 2.6* |
| 4. | Compound IV ($10^{-4}$ M) | 99.5 ± 12.0 | 2.9 ± 1.6* |
| 5. | Compound IV ($10^{-5}$ M) | 113.5 ± 2.7 | 0 |
| 6. | Compound IV ($10^{-6}$ M) | 90.0 ± 1.8 | 3.9 ± 0.6 |
| 7. | Compound IV ($10^{-7}$ M) | 76.7 ± 1.5 | 9.1 ± 0.8 |
| 8. | Glutaryl histamine ($10^{-3}$ M) | 9.3 ± 5.5 | 31.6 ± 6.33 |
| 9. | Glutaryl histamine ($10^{-4}$ M) | 24.1 ± 1.1 | 25.3 ± 3.38 |
| 10. | Glutaryl histamine ($10^{-5}$ M) | 0 | 29.8 ± 6.73 |
| 11. | Control 2 | 100 | 0 |
| 12. | Ovalbumin 1% (max degranulation) | 0 | 38.9 ± 8.43 |
| 13. | Compound V ($10^{-3}$ M) | 10.6 ± 7.6 | 35.3 ± 7.29 |
| 14. | Compound V ($10^{-4}$ M) | 18.9 ± 11.8 | 31.2 ± 6.8 |
| 15. | Compound V ($10^{-5}$ M) | 44.0 ± 11.27 | 24.6 ± 10.38 |
| 16. | Hydrocortisone ($10^{-3}$ M) | 71.0 ± 1.6 | 10.0 ± 0.7 |
| 17. | Hydrocortisone ($10^{-4}$ M) | 48.0 ± 0.8 | 17.3 ± 0.9 |

TABLE 3-continued

In vitro inhibition of OA-induced basophil degranulation of guinea pig blood as effected by compounds of general formula I

| Order No of test | Groups | Complete degranulation inhibition (CDI), (%) | Number of completely degranulated basophils, (%) |
|---|---|---|---|
| 18. | Hydrocortisone ($10^{-5}$ M) | 40.0 ± 0.6 | 20.0 ± 1.3 |

(*P < 0.001)

The data of Table 3 show that as compared to glutaryl histamine, the compound (N) exerts a pronounced anti-anaphylactic action manifested by a practically 100% degranulation inhibition in the test of a complete OA-induced degranulation of blood basophils collected in immunized guinea pigs (in vitro anaphylaxis reaction in a calcium free medium). A significant anti-anaphylactic effect of compound IV is also manifested by decrease in the number of degranulated cells, especially pronounced at concentration 10 M (absence of degranulated cells).

Example 15

Study of the Effect of Compounds of General Formula I on Systemic Anaphylaxis In Vivo A bronchial spasm model in conscious guinea pigs actively sensitized by exposure to aerosol ovalbumin as an antigen was used [Kovaleva V. L. "Metodicheskiye ukazaniya po izucheniyu bronkholiticheskikh I protivovospalitel'nykh sredstv.//Rukovodstvo po experimental'nomy (doklinicheskomu) izucheniyu novykh pharmacologicheskikh veshchestv, Moscow. 2000. pp. 242-250].

Guinea pigs were sensitized by ovalbumin according to the method of Andersson [Anderson P. Antigen-induced bronchial anaphylaxis in actively sensitized guinea-pigs.//Allergy. 1980. Vol. 35. P. 63-71] and in 1-2 months following sensitization, bronchial spasm was induced by aerosol administration of albumin booster dose (3 mg/kg in 1 ml normal saline).

In test groups, guinea pigs were for three days administered with tested compounds at doses 10 μg/kg, 50 μg/kg, and 150 μg/kg, using a probe. In the other group of experiments, the tested compounds at dose 50 μg/kg (in 1 ml normal saline) were administered nasally (using a nebulizer) also once daily for three days. The control group was administered with normal saline. One hour post the last administration of substances, ovalbumin was administered by inhalation using a nebulizer, and intensity and duration (in seconds) of bronchial spasm reaction in animals was assessed.

TABLE 4

Inhibition of systemic anaphylactic reaction of guinea pigs in administering by inhalation of compound IV at dose 50 μg/kg

| Groups | Duration of acute phase, seconds | Duration of sub-acute phase, seconds |
|---|---|---|
| Control 1 (normal saline) | 180 ± 6 | 650 ± 34 |
| Compound IV 50 μg/kg | 0 | 400 ± 25 |

TABLE 5

Inhibition of systemic anaphylactic reaction of guinea pigs in intragastric administering compound IV at doses 10 and 150 μg/kg (M ± m)

| Groups | Duration of acute phase, seconds | Total reaction time, seconds |
|---|---|---|
| Control 2 (normal saline) | 296.7 ± 104.6 | 628.3 ± 80.6 |
| Compound IV 10 μg/kg | 68.0 ± 54.7* | 428.0 ± 75.0 |
| Compound IV 150 μg/kg | 72.0 ± 42.1* | 337.0 ± 78.5* |

*P < 0.001

Experimental results presented in Tables 4 and 5 show that compound IV in intragastric administration at doses 10 and 150 μg/kg and at dose 50 μg/kg by inhalation exhibited anti-anaphylactic activity. Administering the substance at dose 50 μg/kg by inhalation blocked the development of the acute phase of bronchoconstrictory reaction which by inducing suffocation, is a cause of animals' death. In intragastric administration of compound IV at doses 10 and 150 μg/kg, a significant protective effect with regard to antigen-induced bronchial spasm was detected.

Thus, compound IV exhibits a significant protective effect with regard to systemic anaphylactic reaction in vivo.

Example 16

Anti-Allergic Action of Compounds of General Formula I on the Model of Allergic Rhinitis in Guinea Pigs The model of allergic rhinitis in guinea pigs was used.

Guinea pigs were immunized according to the certain scheme for 1.5-2 months (Hutson P. A., Church M. K. et al. 1988): the animals were first immunized by intraperitoneal administration of ovalbumin at dose 10 mg/kg at 7-day interval (twice), then ovalbumin solution was inhaled to the guinea pigs using the Pari nebulizer at increasing concentration beginning from 0.1% and reaching 1% at 4-day intervals between inhalations. The last ovalbumin dose was administered into the nasal passages using a micropipette. 24 hours post the last ovalbumin administration nasal washing was collected (through a system of special tubes) and changes in nasal mucosa was assessed using a complex of histological and cytological methods. The compounds tested (0.1% solution) were daily administered in the form of inhalations using nebulizing device for 6 days; at day 6 of administration, antigen (OA) challenge was performed. Nasal wash-off was obtained 24 hours post challenge.

TABLE 6

The effect of compound IV on cytosis (absolute number of cells in 1 μl) in a nasal wash-off

| Group N | Intact control 6 | Model + challenge (rhinitis) 7 | Compound IV (0.1% solution) 7 |
|---|---|---|---|
| Cytosis | 18.0 ± 2.10 | 67.2 ± 6.47** | 43.7 ± 6.65°* |

*difference from the intact control;
°difference from the model
(°P < 0.05; *P < 0.01; **P < 0.001)

TABLE 7

The effect of compound IV on citogram parameters (%) of a nasal wash-off of guinea pigs

| Group Subpopulation | Intact control n = 6 | Model (rhinitis) n = 7 | Compound IV (0.1% solution) n = 7 |
|---|---|---|---|
| Macrophags | 21.8 ± 1.64 | 12.7* ± 1.57 | 14.6* ± 1.27 |
| Lymphocytes | 4.7 ± 0.88 | 6.1 ± 1.42 | 5.7 ± 1.54 |
| Neutrophils | 0.3 ± 0.21 | 3.3* ± 0.80 | 7.8**° ± 1.35 |
| Eosinophils | 7.0 ± 2.45 | 47.9*** ± 5.37 | 6.9°°° ± 1.32 |
| Epitheliocytes | 66.2 ± 3.09 | 27.1*** ± 5.01 | 63.6°°° ± 3.02 |

*difference from the intact control;
°difference from the model
(°$P < 0.05$; ,°°$P < 0.01$; *,°°°$P < 0.001$)

TABLE 8

The effect of compound IV on absolute number of cellular subpopulations of nasal wash-off of guinea pigs (in 1 μl)

| Group Subpopulation | Intact control n = 6 | Model (rhinitis) n = 7 | Compound IV (0.1% solution) n = 7 |
|---|---|---|---|
| Macrophags | 6.2 ± 1.29 | 7.9 ± 1.88 | 6.1 ± 0.75 |
| Lymphocytes | 0.9 ± 0.24 | 4.1* ± 1.16 | 3.2* ± 52 |
| Neutrophils | 0.03 ± 0.021 | 2.1 ± 0.67 | 3.1 ± 1.02 |
| Eosinophils | 1.2 ± 0.46 | 26.5*** ± 4.47 | 3.2°° ± 0.97 |
| Epitheliocytes | 11.8 ± 1.4 | 11.3 ± 2.10 | 26.3**°° ± 4.31 |

Note:
*difference from the intact control;
°difference from the model
(*$P < 0.05$; ,°°$P < 0.01$; *$P < 0.001$)

It follows form Tables 5-7 that under the conditions of modeling allergic rhinitis, compound IV significantly suppresses eosinophilic inflammation. This is supported by lowering down to the norm absolute and relative number of eosinophils, as well as by a significant lowering cytosis in nasal wash-off.

Example 17

Anti-Allergic Activity of Compounds of General Formula I in the Model of Allergic Pneumonitis in Guinea Pigs The model of allergic pneumonitis in guinea pigs was used.

Immunization of the animals was similar to that described in Example 7.

24 hours post the last ovalbumin administration broncho-alveolar wash-off was collected (through a cannula inserted into the trachea), and changes in bronchial mucosa was assessed using a complex of histological and cytological methods.

The compounds tested (0.1% solution) were daily administered in the form of inhalations using a nebulizing device for 6 days; at day 6 of administration, antigen (OA) challenge was performed.

TABLE 9

The effect of compound IV on cytosis (absolute number of cells in 1 μl) in broncho-alveolar wash-off

| Group N | Intact control 6 | Model + challenge (rhinitis) 5 | Compound IV (0.1% solution) 7 |
|---|---|---|---|
| Cytosis | 726.8 ± 82.4 | 1849.4 ± 287.3* | 1331.3 ± 277.4 |

*$P < 0.01$ - difference from the intact control

TABLE 10

The effect of compound IV on absolute number of cellular subpopulations in broncho-alveolar wash-off of guinea pigs (in 1 μl)

| Group Subpopulation | Intact control | Model | Compound IV (0.1% solution) |
|---|---|---|---|
| Macrophags | 502.6 ± 60.31 (n = 6) | 680.3 ± 105.0 (n = 5) | 640.1 ± 57.98 (n = 6) |
| Lymphocytes | 101.4 ± 24.3 (n = 6) | 328.3** ± 49.18 (n = 5) | 233.0* ± 45.77 (n = 7) |
| Neutrophils | 0 (n = 6) | 56.8 ± 17.08 (n = 5) | 16.9° ± 4.22 (n = 7) |
| Eosinophils | 37.0 ± 9.04 (n = 5) | 773.0** ± 171.7 (n = 5) | 487.4** ± 98.70 (n = 6) |
| Epitheliocytes | 16.9 ± 6.09 (n = 6) | 0 (n = 5) | 2.48* ± 1.84 (n = 7) |

*difference from the intact control;
°difference from the model
(*,°$P < 0.05$; **$P < 0.01$)

It follows from the data of Tables 9 and 10 that compound IV under the conditions of allergic pneumonitis model significantly inhibits inflammatory process that is manifested by decrease in cytosis, lowering the level of the key inflammatory cells eosinophils, by a sharp lowering neutrophil level as well as by decrease in lymphocyte number.

Example 18

Study of Anti-Inflammatory Action of Compounds of General Formula I on the Model of Pneumonitis Induced in Rats by Sephadex The Model of Sephadex-Induced (6-Day) Pneumonitis in Rats Male Wistar rats weighing 270-300 g were used in the tests.

Inflammation in the lungs was induced by a single inhalation of sephadex A-25 (hydrophilic powder with particle sizes from 20 to 80 μm) at dose 5 mg/kg using a dosing device which is a laboratory analog of the inhaler "Cyclohaler" (the Scientific-Research Institute for Pulmonology of the RF).

A Technique of Inhalation Administering Sephadex and Pharmacological Substances

Sephadex A-25 at dose 5 mg per 1 kg body weight was administered to rats under ester anesthesia using an original dosing device for inhalation administering dry powders. Following administration of Sephadex A-25, Wistar rats rapidly recovered form anesthesia, and no peculiarities in their behavior and respiration character were noted. The substances in the form of a dry powder were administered by inhalation at dose 500 μg/kg 1 hour post Sephadex administration, then for 5 days in succession once daily at one and the same morning hours. The control was represented by two groups: a group of intact animals, and a group of rats administered once with Sephadex by inhalation.

The results of therapeutic action of pharmacological substances on pneumonitis development were assessed using morphological and morphometric parameters (volume density and alveolitis) 6 days post aerosol Sephadex administration.

Methods Used in the Study

Histological Method

Histological examinations of the lungs stained by hematoxyline and cosine.

Morphometric Methods 4-5 μm thick histological lung slices were prepared wherein neutrophil number was calculated as well as volume density of alveolitis and emphysema was assessed using the Avtandilov's mesh [Avtandilov G. G., Vvedeniye v kolichestvennuyu pathologicheskuyu morphologiyu.//Moscow. "Meditsina" publishers. 1980. p. 203]. Morphometric examination of pulmonary lymphoid tissue was also carried out. To this end, micro preparations of the lungs were fixed according to the method of Beinenstock et al [Bienenstock J., Johnson N., Perey D. Y. E. Bronchial lymphoid tissue 1. Morphologic characteristics//Lab. Invest. 1973. v. 28 p. 693-698.] The lungs with trachea were removed from the thoracic cavity, and the micro preparation was placed into 2% water acetic acid solution. 18-24 hours later, the trachea, the main and lobular bronchi were dissected, and morphometric assessment of volume density of the lymphoid tissue associated with the bronchi was carried out using the point calculation method under a magnifying glass (magnification ×7). Volume density of alveolitis and emphysema was determined using the point calculation method.

Cytological Methods

Broncho-alveolar wash-off was obtained in rats and guinea pigs under hexenal anesthesia by double washing the lungs through the trachea with 10 ml normal saline. Viability of cells was determined in the test with tryptane blue. Absolute number of cells in 1 ml (cytosis) was determined in the broncho-alveolar wash-off liquid (BAW) using the Goryaev's chamber. In the smears of the BAW liquid precipitate obtained using centrifugation at 200 g for 10 minutes and then stained according to Romanovsky-Gimza, endopulmonary cytogram was calculated (in percent) [Avtsyn A. P., Lukomskij G. I., Romanova L. K. et al. Endopul'monal'naya cytogrammal/Soy. Med. 1982. No 7. pp. 8-14].

The study results were processed using variation statistics method and the Student's t-test

TABLE 11

Broncho-alveolar wash-off cytosis parameters of Wistar rats following aerosol exposure to Sephadex A-25 and treatment with pharmacological agents (M ± m)
Cytosis
Absolute number of cells in 1 μl BAW

| Criterion | Intact control n = 5 | Sephadex (model) n = 6 | Compound IV n = 6 |
|---|---|---|---|
| Cytosis | 160.4 ± 20.65 | 259.2* ± 32.42 | 178.6* ± 20.4 |
| P | | 0.05 | 0.05 |

Note:
*difference from the intact control

TABLE 12

Broncho-alveolar wash-off cytosis parameters of Wistar rats following aerosol exposure to Sephadex A-25 and treatment with pharmacological agents (M ± m)
Cytosis
Absolute number of cells in 1 μl BAW

| Subpopulation N | Intact control 4 | Model (Sephadex) 5 | Compound IV 6 |
|---|---|---|---|
| Macrophags | 124.8 ± 16.35 | 226.1* ± 30.83 | 152.4 ± 18.5 |
| Lymphocytes | 15.5 ± 4.27 | 28.2 ± 6.01 | 22.0* ± 3.5 |
| Neutrophils | 0 | 20.4* ± 6.38 | 5.1* ± 0.6 |

Note:
*difference from the intact control (P < 0.05)

Histological Examination of the Lungs

Compound IV induced a distinct anti-inflammatory action: prevalence of alveolitis was significantly lower as compared to the model group of animals; emphysema was not practically detected; infiltration of interalveolar septa with neutrophils was not noted. By cytosis level and number of neutrophils in the BAW, inflammatory process was also significantly less pronounced that in animals administered with Sephadex for 5 days.

Thus, all complex of the experimental models used suggests a significant anti-allergic, anti-anaphylactic and anti-inflammatory activity of compounds of general formula I manifested in both in vitro tests and in modeling allergic and inflammatory pathology in vivo.

Example 19

The Study of Hypolipidemic Action of Compounds of General Formula I on the Model of Hypercholesterolemia in Rats The study was carried out on male Wistar rats weighing 200±20 g. Hyperlipidemia was induced by oral administration of cholesterol loading, oily cholesterol suspension:

olive oil (Acorsa, Spain)—5 ml/kg weigh of animals;

cholesterol (Sigma, USA)—1 g/kg weight;

sodium cholate (Sigma, USA)—100 mg/kg weight.

As a reference preparation, the preparation from the group of statines "Mevacor" (Lovastatine) manufactured by the firm Merck Sharp & Dohn was used at dose 40 mg/kg. Cholesterol suspension was administered daily in the morning for 10 days. The compounds tested (at dose 500 μg/kg) and the reference preparation (at dose 40 mg/kg) were administered to the animals togester with cholesterol suspension for 10 days. All the animals received a standard briquetted forage.

The animals were divided into the following groups:

"Control"—intact animals (n=6);

"Cholesterol"—rats that orally received cholesterol loading (n=10);

"Lovastatine"—rats that orally received cholesterol loading and Lovastatine (n=10);

"Compound IV"—rats that orally received cholesterol loading and the tested compound IV (n=10).

Blood was sampled at days 5, 8 and 10 of the experiment.

Statistical processing of the hypolipidemic action data of the tested substances was carried out with regard to the "Cholesterol" group (Table 13).

TABLE 13

Cholesterol and triglyceride level in blood serum and liver of rats orally administered for 10 days with olive oil, cholesterol and compound IV concurrently with cholesterol loading

|  | Control (n = 6) | Cholesterol (n = 10) | Lovastatine (n = 10) | Compound IV (n = 9) |
|---|---|---|---|---|
| Total cholesterol |  |  |  |  |
| Serum (mg/100 ml) | 67.2 ± 6.1 | 120.0 ± 8.4 | 100.5 ± 6.7* | 96.6 ± 5.7** |
| CHDL (mg/100 ml) | 41.6 ± 1.3 | 54.3 ± 1.7 | 50.6 ± 1.3 | 50.5 ± 1.3* |
| CLLD + CLVLD (mg/100 ml) | 25.6 ± 0.8 | 65.7 ± 1.2 | 49.9 ± 0.9*** | 46.1 ± 0.9*** |
| Liver (mg/g of tissue) | 2.29 ± 0.13 | 3.6 ± 0.4 | 2.41 ± 0.17*** | 2.78 ± 0.28*** |
| TRIGLYCERIDS |  |  |  |  |
| Serum (mg/100 ml) | 85.7 ± 9.2 | 99.2 ± 8.7 | 93.6 ± 7.5 | 95.1 ± 7.9 |
| Liver (mg/g of tissue) | 3.89 ± 0.14 | 6.83 ± 0.39 | 6.25 ± 0.13 | 5.53 ± 0.19*** |

*p < 0.1
**p < 0.05
***p < 0.01

Administering compound IV at dose 500 µg/kg resulted in a significant lowering serum total cholesterol by 19.5%, hepatic cholesterol by 22.7%, LDL cholesterol by 29.8% and hepatic triglycerides by 19%. The compound glutaryl histamine, by lowering total cholesterol level only by 9%, exerted effect only on LDL and VLDL (low and very; low density lipoproteins) that is shown in the publication of the International application WO 99/01103, and it is apparently less efficient than compound IV in a similar biological experiment.

The study results of the other claimed compounds are presented below.

Experimental groups included:
1) "Cholesterol"—rats orally administered with oily cholesterol suspension for 10 days;
2) "Compound IV"—rats orally administered with oily cholesterol suspension and the tested compound IV;
3) "Compound IV—1Na"—rats orally administered with oily cholesterol suspension and the tested mono-sodium salt of compound IV;
4) "Compound IV—2Na"—rats orally administered with oily cholesterol suspension and the tested di-sodium salt of compound IV;
5) "Compound V—1Na"—rats orally administered with oily cholesterol suspension and the tested mono-sodium salt of the compound V;
6) "Compound III—1Na"—rats orally administered with oily cholesterol suspension and the tested mono-sodium salt of the compound III;
7) "Compound II—1Na"—rats orally administered with oily cholesterol suspension and the tested mono-sodium salt of the compound II;
8) "Sim"—rats orally administered with oily cholesterol suspension and Simvastatine;
9) control—intact rats before beginning the test.

At day 10 of the test blood samples were taken following decapitation of the animals. The animals fasted for 12 hours prior to decapitation.

Blood serum total cholesterol, triglycerides and high density lipoprotein cholesterol (HDLC) were measured. Low and very low density lipoprotein cholesterol was calculated by the difference between total cholesterol and HDL cholesterol.

Blood serum total cholesterol and triglycerides were determined using the enzymatic methods.

Cholesterol level in high density lipoproteins (α-LP) was determined using the precipitation method of LDL and VLDL with phosphotungstic acid and magnesium ions.

Statistical Processing

Data in the tables are presented as a mean value±standard error. Significance of differences between the groups "cholesterol" and "preparation . . . " was assessed by the two-sampled Student's t-test. Error probability (p) is indicated in the table graphs.

The data on the effect of the compounds on blood serum cholesterol and triglyceride levels of rats that received cholesterol loading are presented in Tables 14 to 21.

TABLE 14

Experimental hypercholesterolemia
Lipid metabolism parameters in rats (mg/100 ml)

|  | Prior to beginning of experiment (n = 50) | 10 days of cholesterol loading (n = 20) |
|---|---|---|
| Total cholesterol |  |  |
| Serum | 59.9 ± 1.4 | 135.7 ± 10.9 |
| HDL | 38.2 ± 1.2 | 32.5 ± 1.1 |
| LDL + VLDL | 20.3 ± 1.3 | 103.2 ± 11.5 |
| Triglycerides |  |  |
| Serum | 83.6 ± 4.6 | 156.6 ± 11.4 |
| HDL | 19.0 ± 1.4 | 24.3 ± 1.8 |
| LDL + VLDL | 58.7 ± 6.2 | 132.6 ± 12.8 |

10-day administering oily cholesterol suspension to rats resulted in a significant 2,3-fold rise in serum cholesterol level and in 1.9-fold rise in triglyceride levels. In the development of induced hyperlipidemia, HDL cholesterol lowered by 15%. 5-fold rise in LDL+VLDL cholesterol was observed. 2.3-fold rise in LDL+VLDL triglycerides was observed.

TABLE 15

Blood serum cholesterol and triglyceride levels
(mg/100 ml) in rats at day 5 of the experiment

| Total cholesterol | "Cholesterol" (n = 20) | "Compound IV" (n = 20) | "Compound IV-1Na" (n = 20) | "Compound IV" 2Na" (n = 19) | "Sim" (n = 10) |
|---|---|---|---|---|---|
| Serum | 92.3 ± 3.5 | 84.2 ± 3.9 | 72.0 ± 3.0 p = 0.0001 | 80.6 ± 2.8 p = 0.013 | 73.6 ± 7.3 p = 0.04 |
| HDL | 34.3 ± 1.3 | 35.8 ± 1.2 | 33.1 ± 1.4 | 35.0 ± 1.3 | 27.8 ± 2.7 |
| LDL + VLDL | 58.0 ± 4.1 | 48.5 ± 4.5 | 38.8 ± 2.9 p = 0.0006 | 44.3 ± 2.7 p = 0.02 | 43.0 ± 8.3 |
| Triglycerides Serum | 110.8 ± 7.1 | 120.6 ± 8.9 | 106.6 ± 6.2 | 88.3 ± 4.8 p = 0.013 | 108.9 ± 6.9 |

TABLE 16

Blood serum cholesterol and triglyceride levels
(mg/100 ml) in rats at day 8 of the experiment

| Total cholesterol | "Cholesterol" (n = 20) | "Compound IV" (n = 20) | "Compound IV" 1Na" (n = 20) | "Compound IV" 2Na" (n = 19) | "Sim" (n = 10) |
|---|---|---|---|---|---|
| Serum | 127.2 ± 10.6 | 103.3 ± 8.1 p = 0.08 | 99.1 ± 6.0 p = 0.03 | 90.2 ± 5.1 p = 0.004 | 100.1 ± 12.8 |
| HDL | 30.2 ± 1.0 | 35.9 ± 1.2 p = 0.0007 | 37.1 ± 1.4 p = 0.0003 | 35.9 ± 1.8 p = 0.01 | 33.2 ± 1.8 |
| LDL + VLDL | 97.0 ± 11.3 | 67.3 ± 8.7 p = 0.04 | 61.9 ± 6.6 p = 0.01 | 54.3 ± 5.8 p = 0.002 | 66.9 ± 13.4 p = 0.1 |
| Triglycerides Serum | 150.6 ± 13.6 | 154.2 ± 11.4 | 146.4 ± 11.2 | 125.8 ± 9.4 | 119.9 ± 10.5 p = 0.085 |

TABLE 17

Blood serum cholesterol and triglyceride levels
(mg/100 ml) in rats at day 10 of the experiment

| Total cholesterol | "Cholesterol" (n = 20) | "Compound IV" (n = 20) | "Compound IV" 1Na" (n = 20) | "Compound IV" 2Na" (n = 19) | "Sim" (n = 10) |
|---|---|---|---|---|---|
| Serum | 135.7 ± 10.9 | 95.2 ± 5.4 p = 0.003 | 97.4 ± 7.1 p = 0.006 | 97.9 ± 3.9 p = 0.003 | 93.9 ± 10.2 p = 0.01 |
| HDL | 32.5 ± 1.1 | 36.5 ± 0.9 p = 0.093 | 37.7 ± 1.0 p = 0.02 | 40.0 ± 1.9 p = 0.002 | 32.7 ± 1.2 |
| LDL + VLDL | 103.2 ± 11.5 | 58.7 ± 5.3 p = 0.002 | 59.7 ± 7.2 p = 0.003 | 57.3 ± 4.3 p = 0.002 | 61.2 ± 9.7 p = 0.01 |
| Triglycerides Serum | 156.6 ± 11.4 | 143.3 ± 8.9 | 132.5 ± 8.4 p = 0.096 | 127.3 ± 6.2 p = 0.03 | 142.0 ± 5.4 |

TABLE 18

Hypercholesterolemia development in experimental animals in the "Cholesterol" group

| Parameters | Lipid metabolism parameters (mg/100 ml)* | | | |
|---|---|---|---|---|
| | Prior to beginning the experiment (n = 30) | 5 days of cholesterol loading (n = 12) | 8 days of cholesterol loading (n = 12) | 10 days of cholesterol loading (n = 12) |
| Total cholesterol | | | | |
| Serum | 89.1 ± 1.8 | 112.9 ± 9.2<br>p = 0.025 | 153.0 ± 14.7 | 144.6 ± 12.8 |
| HDL | 66.7 ± 1.1 | 47.5 ± 3.7<br>p < 0.02 | 50.3 ± 5.1 | 46.7 ± 2.9 |
| LDL + VLDL | 22.5 ± 1.7 | 65.4 ± 10.6<br>p < 0.001 | 100.9 ± 17.3 | 97.9 ± 14.0 |
| Triglycerides | | | | |
| Serum | 74.8 ± 4.1 | 94.5 ± 9.2 | 129.7 ± 17.9 | 115.8 ± 18.9 |
| HDL | 43.1 ± 1.9 | 35.0 ± 3.1<br>p < 0.05 | 46.0 ± 4.6 | 35.5 ± 3.1 |
| LDL + VLDL | 31.7 ± 3.7 | 59.5 ± 7.6<br>p < 0.05 | 76.0 ± 14.7 | 80.3 ± 16.2 |

10-day administering oily cholesterol suspension to rats resulted in a significant 1.7-fold rise in serum total cholesterol and 1.6-fold rise in triglycerides level (Table 18). HDL cholesterol lowered by 28% from the initial 66.7 down to 48 mg/100 ml in the development of induced hyperlipidemia. 4.4-fold LDL+VLDL cholesterol level rise from 22.5 to 99 mg/100 ml was observed.

TABLE 19

Blood serum cholesterol and triglyceride levels (mg/100 ml) in rats at day 5 of the experiment

| Parameters | Groups | | | | |
|---|---|---|---|---|---|
| | "Cholesterol" (n = 12) | "Compound IV-1Na" (n = 12) | "Compound V-1Na" (n = 12) | "Compound III-1Na" (n = 12) | "Compound II-1Na" (n = 12) |
| Total cholesterol | | | | | |
| Serum | 112.9 ± 9.2 | 94.4 ± 3.4<br>p = 0.079 | 96.9 ± 4.5 | 89.0 ± 5.0<br>p = 0.035 | 109.7 ± 9.4 |
| HDL | 47.5 ± 3.7 | 60.7 ± 3.1<br>p = 0.012 | 55.1 ± 2.8<br>p = 0.11 | 49.0 ± 2.1 | 49.5 ± 3.8 |
| LDL + VLDL | 65.4 ± 10.6 | 33.7 ± 4.5<br>p = 0.015 | 41.7 ± 6.5<br>p = 0.073 | 40.0 ± 5.4<br>p = 0.048 | 60.2 ± 10.6 |
| Triglycerides | | | | | |
| Serum | 94.5 ± 9.2 | 83.2 ± 6.3 | 63.3 ± 5.4<br>p = 0.009 | 87.4 ± 9.4 | 80.9 ± 5.5 |
| HDL | 35.0 ± 3.1 | 39.4 ± 3.5 | 30.9 ± 1.8 | 30.0 ± 2.2 | 32.6 ± 2.5 |
| LDL + VLDL | 59.5 ± 7.6 | 43.7 ± 4.6<br>p = 0.09 | 32.4 ± 4.4<br>p = 0.007 | 57.4 ± 9.1 | 48.2 ± 4.9 |

TABLE 20

Blood serum cholesterol and triglyceride levels
(mg/100 ml) in rats at day 8 of the experiment

| Parameters | "Cholesterol" (n = 12) | "Compound IV-1Na" (n = 12) | "Compound V-1Na" (n = 12) | "Compound III-1Na" (n = 12) | "Compound II-1Na" (n = 12) |
|---|---|---|---|---|---|
| Total cholesterol | | | | | |
| Serum | 153.0 ± 14.7 | 120.8 ± 4.3 p = 0.07 | 124.8 ± 5.8 p = 0.11 | 108.8 ± 8.2 p = 0.03 | 140.8 ± 13.6 |
| HDL | 50.3 ± 5.1 | 54.9 ± 2.4 | 54.2 ± 3.4 | 48.4 ± 2.7 | 52.9 ± 4.1 |
| LDL + VLDL | 100.9 ± 17.3 | 65.0 ± 6.0 p = 0.09 | 70.6 ± 6.8 p = 0.14 | 60.4 ± 8.3 p = 0.06 | 87.9 ± 14.5 |
| Triglycerides | | | | | |
| Serum | 129.7 ± 17.9 | 116.3 ± 10.5 | 95.4 ± 5.7 p = 0.12 | 124.4 ± 8.9 | 111.6 ± 17.2 |
| HDL | 46.0 ± 4.6 | 45.8 ± 2.3 | 42.2 ± 2.1 | 45.2 ± 3.2 | 44.5 ± 2.5 |
| LDL + VLDL | 76.0 ± 14.7 | 70.5 ± 9.0 | 53.2 ± 4.6 | 79.2 ± 7.7 | 73.9 ± 15.4 |

TABLE 21

Blood serum cholesterol and triglyceride levels
(mg/100 ml) in rats at day 10 of the experiment

| Parameters | "Cholesterol" (n = 12) | "Compound IV-1Na" (n = 12) | "Compound V-1Na" (n = 12) | "Compound III-1Na" (n = 12) | "Compound II-1Na" (n = 11) |
|---|---|---|---|---|---|
| Total cholesterol | | | | | |
| Serum | 144.6 ± 12.8 | 122.1 ± 9.8 p = 0.18 | 123.3 ± 7.3 p = 0.18 | 102.3 ± 6.9 p = 0.014 | 134.4 ± 12.5 |
| HDL | 46.7 ± 2.9 | 53.4 ± 2.2 p = 0.09 | 52.9 ± 3.8 | 48.8 ± 2.4 | 54.7 ± 2.2 p = 0.046 |
| LDL + VLDL | 97.9 ± 14.0 | 68.7 ± 10.1 p = 0.11 | 70.5 ± 8.9 p = 0.12 | 53.5 ± 7.3 p = 0.02 | 79.7 ± 12.6 |
| Triglycerides | | | | | |
| Serum | 115.8 ± 18.9 | 109.3 ± 5.1 | 81.9 ± 4.4 p = 0.11 | 109.3 ± 10.5 | 108.5 ± 11.3 |
| HDL | 35.5 ± 3.1 | 36.2 ± 2.6 | 31.5 ± 1.8 | 34.3 ± 2.3 | 38.9 ± 2.4 |
| LDL + VLDL | 80.3 ± 16.2 | 73.1 ± 5.2 | 50.4 ± 4.8 p = 0.1 | 75.0 ± 8.5 | 69.6 ± 11.1 |

Administering a mono-sodium salt of compound III to the animals significantly lowered total cholesterol (CH) by 29% and cholesterol of the VLDL+LDL fractions by 40%, but it did not change the level of CH of serum anti-atherogenic HDL and total triglycerides.

The results obtained suggest that mono- and di-sodium salts were superior over compound IV by action dynamics on serum total cholesterol and LDL+VLDL cholesterol and other parameters of lipid metabolism. Whereas by day 10 of the experiment, a significant and comparable lowering the mentioned parameters occurred under the effect of all the compounds mentioned above and the reference preparation "Zokor" (Simvastatine), salt of compound N begun action at earlier terms of the experiment (by days 5 and 8). The both sodium salts of compound N elevated HDL already by day 5 of the experiment, whereas compound IV elevated this parameter only by day 8. The reference preparation Simvastatine did not effect HDL cholesterol. Furthermore, disodium salt of compound IV lowered serum total triglyceride levels at days 5 and 10 of the experiment.

A distinguishing feature of the compound V mono-sodium salt was the ability thereof to lower serum total triglyceride levels, whereas lowering total cholesterol and VLDP cholesterol levels and rise in HDL level were lower than in the compound III and compound N mono-sodium salts.

Thus, as compared to the activity of the compounds disclosed in the publication of International application WO 99/01103, and the compounds proposed in the instant invention, salts of the compounds II, III, IV and V possess enhanced hypolipidemic activity including the capability of lowering serum triglyceride, total cholesterol levels including LDL cholesterol level and elevating HDL cholesterol.

Example 19

Study of Hypolipidemic Effect of Compounds of General Formula I on the Model of "Endogenous" Hypercholesterolemia in Guinea Pigs The study was carried out on male guinea pigs (Aguti line) weighing 304±25 g. The experiment lasted 31 days. The control group included 6 guinea pigs (intact animals). The compounds studied were administered from day 1 of the experiment (from day 1 of administering fat loading).

The animals of experimental groups received orally for 31 days a compound studied and fat loading. The compound studied at doses indicated below was administered in the form of an aqueous solution (0.5 ml per an animal); fat loading (a mixture of porcine fat and preliminary heated corn oil at 4:1 ratio by volume, at the rate of 5 ml/kg weight 0.5 h post administering the substance studied.

Experimental groups:

1) "control"—intact animals;

2) "fat"—animals that received fat loading only;

3) "compound IV"—animals that received fat loading+ compound IV at dose 500 µg/kg body weight;

4) "compound V"—animals that received fat loading+ compound V at dose 500 µg/kg body weight.

The data on blood serum cholesterol and triglyceride levels in guinea pigs that received fat loading and the compounds studied, are presented in Tables 22 to 25.

TABLE 22

Blood serum total cholesterol level in guinea pigs that received fat loading and the compounds studied

| | Serum total cholesterol | |
|---|---|---|
| | Day 28 | Day 31 |
| Control | | 37.4 ± 3.3 |
| Fat | 71.7 ± 14.5 | 74.4 ± 11.4 |
| | n = 9 | |
| Compound IV | 55.5 ± 6.3 | 49.2 ± 3.9 |
| | n = 10 | P = 0.064 |
| Compound V | 52.9 ± 6.5 | 46.3 ± 4.1 |
| | n = 9 | P = 0.043 |

Statistical processing was carried out using a mono-factorial analysis of variance.

TABLE 23

Blood serum total triglyceride levels in guinea pigs that received fat loading and the compounds studied

| | Serum total triglyceride levels | |
|---|---|---|
| | Day 28 | Day 31 |
| Control | | 60.1 ± 2.4 |
| Fat | 89.7 ± 14.0 | 123.1 ± 35.6 |
| Compound IV | 66.8 ± 6.7 | 69.0 ± 13.4 |
| Compound V | 62.3 ± 5.4 | 56.0 ± 6.1 |

TABLE 24

Total cholesterol level in lipoprotein fractions at day 31 of blood serum guinea pigs that received fat loading and the compounds studied

| | Cholesterol, mmole/100 ml | | |
|---|---|---|---|
| | Total | VLDL | LDL |
| Control | 38.4 ± 3.3 | 1.6 ± 0.07 | 32.2 ± 2.8 |
| Fat | 74.4 ± 11.4 | 4.1 ± 1.2 | 67.6 ± 10.2 |
| | | | P = 0.009 |
| Compound IV | 49.2 ± 3.9 | 3.0 ± 0.71 | 42.1 ± 3.5 |
| | | | P = 0.040 |
| Compound V | 46.3 ± 4.1 | 2.1 ± 0.4 | 41.9 ± 2.7 |
| | | | P = 0.038 |

TABLE 25

Total triglyceride level in lipoprotein fractions at day 31 of blood serum guinea pigs that received fat loading and the compounds studied

| | Triglycerides, µg/100 ml | | |
|---|---|---|---|
| | Total | VLDL | LDL |
| Control | 60.1 ± 2.36 | 38.16 ± 2.86 | 16.13 ± 0.97 |
| Fat | 123.2 ± 35.6 | 59.5 ± 19.7 | 42.7 ± 8.62 |
| | | | P = 0.015 |
| Compound IV | 69.0 ± 13.4 | 33.2 ± 12.3 | 29.6 ± 2.4 |
| Compound V | 56.0 ± 6.1 | 22.5 ± 4.4 | 23.1 ± 1.9 |
| | P = 0.1 | P = 0.1 | P = 0.053 |

The studied compounds IV and V significantly lowered total cholesterol level by 33.9 and 37.8% respectively only by day 31 of the experiment At the same time, they significantly lowered LDL cholesterol by 37.7 and 38%.

Advantage of the claimed compounds, in particular compound IV, is a broad range of acting doses that provides for broadness of therapeutic effect thereof. Thus, for example, compound IV was practically similarly effective in lowering total cholesterol level during 20 days at interval of doses from 50 to 1,500 µg/kg differing 30-fold.

Thus, the claimed compounds corresponding to general formula I possess a significant hypolipidemic activity considerably improving the lipid metabolism parameters in blood serum and in the liver.

Example 20

Study of Anti-Inflammatory Action of Compounds of General Formula I on the Model of Carrageenan Rat Paw Edema The experiments were performed on white outbred male rats weighing 250 g. A total amount of animals per an experiment was 12.

The model of carrageenan-induced edema according to the method of Winter et al. was used (Winter et al. Studies of the mediators of the acute inflammatory response induced in rats in different sites by carrageenan and turpentine.//J. Phamacol. 1971. V. 104. P. 15-29). 0.1 ml 1% carrageenan solution (SERVA) was subplantarly injected into the right rat paw. The animals were placed into individual chambers. Gel (1%) comprising a substance tested was applied on the paw three times: immediately following carrageenan administration, ate 1 and 2 hours post administration. 4 hours post administration of carrageenan, paw volumes were measured using a plethysmograph (Ugo Basile) Therapeutic effect of the gel was assessed by inhibition degree of inflammatory reaction in comparison with the intact left paw of the given animal and rat paw reaction of the control (untreated) group. Inflammatory reaction inhibition expressed in percent, was calculated according to the formula:

$$\text{Volume gain} = \frac{\text{difference} \times 100}{\text{Left paw volume}}$$

$$\text{Inhibition} = 100 - \frac{\text{Volume gain}_{(experiment)} \times 100}{\text{Volume gain}_{(control)}}$$

The tested compounds VI and XIII in the form of 1% gel caused inhibition of edema by 44% and 40%, respectively, and the reference preparation diclofenac (1% gel) inhibited edema by 62%.

Examples of Dosage Forms

Example 21

A. Tablets

The Tablets are Prepared Using the Ingredients Presented Below:

| | |
|---|---|
| Compound corresponding to general formula I or a pharmaceutically acceptable salt thereof | 1-150 mg |
| Potato starch | 20-50 mgr |
| Magnesium stearate | 3 mg |
| Aerosyl | 1 mg |
| Lactose | up to 300 mg |

The components are mixed and compressed to form tablets weighing 300 mg each.

B. Suppositories

Example of a Suppository Composition:

| | |
|---|---|
| Compound corresponding to general formula I or a pharmaceutically acceptable salt thereof | 1-100 mg |
| Cocoa butter | An amount required to prepare a suppository |

If needed, preparing rectal, vaginal and urethral suppositories with respective excipients is possible.

C. Ointments

Example of Ointment Composition:

| | |
|---|---|
| Compound corresponding to general formula I or a pharmaceutically acceptable salt thereof | 1-500 mg |
| Vaseline | 10 g |

Ointments are prepared according to the generally known technology.

D. Gels

Example of a Gel Composition:

| | |
|---|---|
| Compound corresponding to general formula I or a pharmaceutically acceptable salt thereof | 1-500 mg |
| Carbopol | 200 mg |
| Benzyl alcohol | 20 mg |
| Ethyl alcohol | 300 mg |
| water | Up to 10 g |

E. Dry Powder for Inhalations

Example of a Powder Composition:

| | |
|---|---|
| Compound corresponding to general formula I or a pharmaceutically acceptable salt thereof | 20-200 mg |
| lactose | Up to 1 g |

The powder is filled into a special device (container) or into a gelatin capsule.

F. Nasal Spray

Example of a Spray Composition:

| | |
|---|---|
| Compound corresponding to general formula I or a pharmaceutically acceptable salt thereof | 1.5-150 mg |
| Purified water | Up to 15 ml |

G. Eye Drops

Composition Example of Eye Drops:

| | |
|---|---|
| Compound corresponding to general formula I or a pharmaceutically acceptable salt thereof | 0.5-50 mg |
| preservative | 10 mg |
| Purified water | Up to 5 ml |

H. Solution for Injections

Composition Example of a Solution for Injections:

| | |
|---|---|
| Compound corresponding to general formula I or a pharmaceutically acceptable salt thereof | 0.2-20 mg |
| Water for injections | 2 mg |

The invention claimed is:
1. N-acyl derivatives of amino acids of general formula I

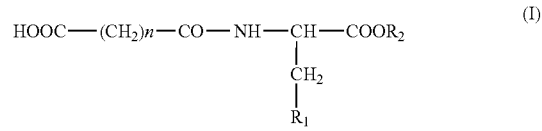

wherein n is 2 or 3; and
$R_1$ represents

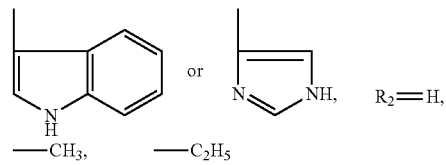

or a pharmaceutically acceptable salt thereof,
with proviso that the compound of general formula I is not succinyl-L-tryptophane, succinyl-D-tryptophane and succinyl-D,L-tryptophane and a dipotassium salt thereof, $N^\alpha$-succinyl-L-tryptophane methyl ester, $N^\alpha$-glutaryl-L-histidine methyl ester, $N^\alpha$-glutaryl-L-tryptophane, $N^\alpha$-glutaryl-L-tryptophane methyl ester, $N^\alpha$-succinyl-L-histidine, $N^\alpha$-glutaryl-D-tryptophane methyl ester, $N^\alpha$-glutaryl-L-histidine, or $N^\alpha$-glutaryl-L-histidine ethyl ester.

2. The compound according to claim 1, wherein the pharmaceutically acceptable salt is a mono- or disodium salt.

3. A pharmaceutical composition comprising an N-acyl derivative of an amino acid of formula I

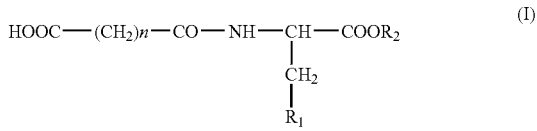

wherein n is 2 or 3; and
$R_1$ represents

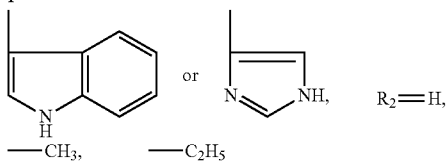

or a pharmaceutically acceptable salt thereof
with proviso that the N-acyl derivative of formula I is not succinyl-L-tryptophane, succinyl-D-tryptophane and succinyl-D,L-tryptophane and a dipotassium salt thereof, $N^\alpha$-succinyl-L-tryptophane methyl ester, $N^\alpha$-glutaryl-L-histidine methyl ester, $N^\alpha$-glutaryl-L-tryptophane methyl ester, $N^\alpha$-succinyl-L-histidine, $N^\alpha$-glutaryl-D-tryptophane methyl ester, $N^\alpha$-glutaryl-L-triptophane, $N^\alpha$-glutaryl-L-histidine, or $N^\alpha$-glutaryl-L-histidine ethyl ester, and a pharmaceutically acceptable additive, wherein the N-acyl derivative or pharmaceutically acceptable salt thereof is present in the composition in an amount effective to possess anti-allergic, anti-anaphylactic, or anti-inflammatory activity.

4. A method for lowering antigen-dependent histamine secretion, basophil degranulation or controlling the level of eosinophils, neutrophils or lymphocytes in a mammal, the method comprising administering to the mammal a compound of claim 1 or a pharmaceutically acceptable salt thereof.

5. A medicament comprising an N-acyl derivative of an amino acid of formula I

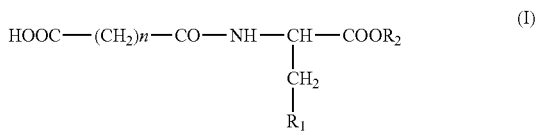

wherein n is 2 or 3; and
$R_1$ represents

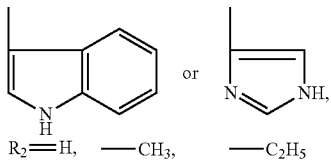

or a pharmaceutically acceptable salt thereof
with proviso that the N-acyl derivative of formula I is not succinyl-L-tryptophane, succinyl-D-tryptophane and succinyl-D,L-tryptophane and a dipotassium salt thereof, $N^\alpha$-succinyl-L-tryptophane methyl ester, $N^\alpha$-glutaryl-L-histidine methyl ester, $N^\alpha$-glutaryl-L-tryptophane methyl ester, $N^\alpha$-succinyl-L-histidine, $N^\alpha$-glutaryl-D-triptophane methyl ester, $N^\alpha$-glutaryl-L-triptophane, $N^\alpha$-glutaryl-L-histidine, or $N^\alpha$-glutaryl-L-histidine ethyl ester, wherein the N-acyl derivative or pharmaceutically acceptable salt thereof is present in the medicament in an amount effective to possess anti-allergic, anti-anaphylactic, anti-inflammatory activity.

6. A method for treating an indication selected from the group consisting of bronchial asthma, psoriasis, atherosclerosis, obesity, ischemic heart disease, ischemic cerebral disease, myocardial infarction, and stroke, comprising administration to a mammal in need of such treatment of an effective amount of the compound of claim 1 or a pharmaceutically acceptable salt thereof.

7. A method for treating an indication selected from the group consisting of allergic rhinitis, pollinoses, seasonal rhinitis, year-round rhinitis, allergic pneumonitis, atopic dermatitis, urticaria, allergic (including anaphylactic) reactions to insect stings and medicaments, cold allergy, and allergic conjunctivitis, comprising administration to a mammal in need of such treatment of an effective amount of the compound of general formula I of claim 1 or a pharmaceutically acceptable salt thereof.

8. A pharmaceutical composition comprising an N-acyl derivative of an amino acid of formula I

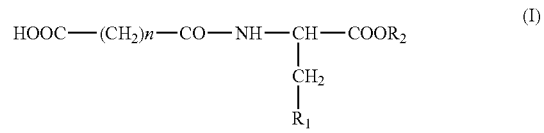

wherein n is 2 or 3; and
$R_1$ represents

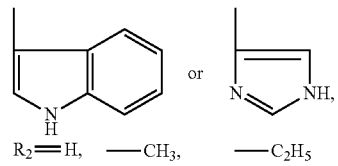

or a pharmaceutically acceptable salt thereof
with proviso that the N-acyl derivative of Formula I is not succinyl-L-tryptophane, succinyl-D-tryptophane and succinyl-D,L-tryptophane and a dipotassium salt thereof, $N^\alpha$-succinyl-L-tryptophane methyl ester, $N^\alpha$-glutaryl-L-histidine methyl ester, $N^\alpha$-glutaryl-L-tryptophane methyl ester, $N^\alpha$-succinyl-L-histidine, $N^\alpha$-glutaryl-D-taryl-D-triptophane methyl ester, $N^\alpha$-glutaryl-L-triptophane, $N^\alpha$-glutaryl-L-histidine, or $N^\alpha$-glutaryl-L-histidine methyl ester and a pharmaceutically acceptable additive wherein the N-acyl derivative or pharmaceutically acceptable salt thereof is present in the composition in an amount effective for lowering antigen-dependent histamine secretion, basophil degranulation and controlling the level of eosinophils, neutrophils and lymphocytes.

9. The pharmaceutical composition of claim 3 for treating bronchial asthma or psoriasis.

10. A pharmaceutical composition comprising an effective amount of the compound of general formula I

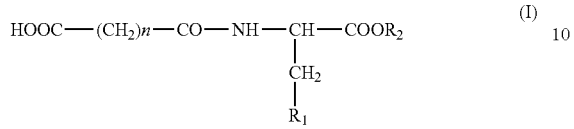

wherein n is 2 or 3; and
$R_1$ represents

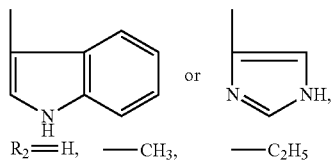

or a pharmaceutically acceptable salt thereof,
with proviso that the compound of general formula I is not succinyl-L-tryptophane, succinyl-D-tryptophane and succinyl-D, L-tryptophane and a dipotassium salt thereof, $N^\alpha$-succinyl-L-tryptophane methyl ester, $N^\alpha$-glutaryl-L-histidine methyl ester, $N^\alpha$-glutaryl-L-tryptophane methyl ester, $N^\alpha$-succinyl-L-histidine, $N^\alpha$-glutaryl-D-triptophane methyl ester, $N^\alpha$-glutaryl-L-triptophane, $N^\alpha$-glutaryl-L-histidine, or $N^\alpha$-glutaryl-L-histidine ethyl ester,
and a pharmaceutically acceptable additive, wherein the compound is present in the composition in an amount effective for treating an indication selected from the group consisting of allergic rhinitis, pollinoses, seasonal rhinitis, -year-round rhinitis, allergic pneumonitis, atopic dermatitis, urticaria, allergic (including anaphylactic) reactions to insect stings, allergic reactions to medicaments, cold allergy, and allergic conjunctivitis.

11. A pharmaceutical composition comprising an N-acyl derivative of an amino acid of general formula I

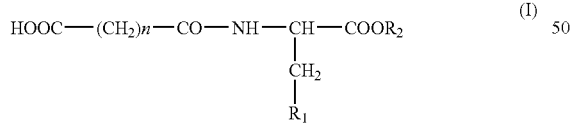

wherein n is 2 or 3; and
$R_1$ represents

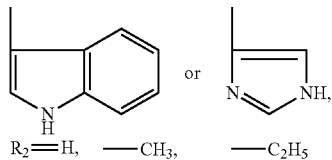

or a pharmaceutically acceptable salt thereof,
with proviso that the N-acyl derivative is not succinyl-L-tryptophane, succinyl-D-tryptophane and succinyl-D,L-tryptophane and a dipotassium salt thereof, $N^\alpha$-succinyl-L-tryptophane methyl ester, $N^\alpha$-glutaryl-L-histidine methyl ester, $N^\alpha$-glutaryl-L-tryptophane methyl ester, $N^\alpha$-succinyl-L-histidine, $N^\alpha$-glutaryl-D-triptophane methyl ester, $N^\alpha$-glutaryl-L-triptophane, $N^\alpha$-glutaryl-L-histidine ethyl ester, and pharmaceutically acceptable additives, wherein the N-acyl derivative or pharmaceutically acceptable salt thereof is present in the composition in an amount effective to possess hypolipidemic activity.

12. The pharmaceutical composition according to claim 11 for wherein the N-acyl derivative or pharmaceutically acceptable salt thereof is present in the composition in an amount effective for treating an indication selected from the group consisting of atherosclerosis, obesity, ischemic heart disease, ischemic cerebral disease, myocardial infarction, and stroke.

13. A medicament comprising an N-acyl derivative of an amino acid of general formula I

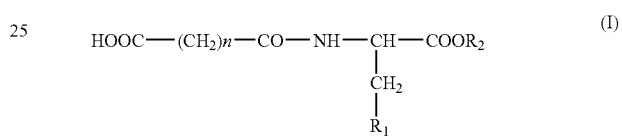

wherein n is 2 or 3; and
$R_1$ represents

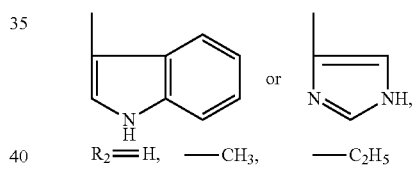

or a pharmaceutically acceptable salt thereof,
with proviso that the compound of general formula I is not succinyl-L-tryptophane, succinyl-D-tryptophane and succinyl-D,L-tryptophane and a dipotassium salt thereof, $N^\alpha$-succinyl-L-tryptophane methyl ester, $N^\alpha$-glutaryl-L-histidine methyl ester, $N^\alpha$-glutaryl-L-tryptophane methyl ester, $N^\alpha$-succinyl-L-histidine, $N^\alpha$-glutaryl-D-triptophane methyl ester, $N^\alpha$-glutaryl-L-triptophane, $N^\alpha$-glutaryl-L-histidine ethyl ester, wherein the N-acyl derivative or pharmaceutically acceptable salt thereof is present in the medicament in an amount effective to possess hypolipidemic activity.

14. A compound selected from the group consisting of $N^\alpha$-glutaryl-L-histidine monosodium salt and $N^\alpha$-glutaryl-L-histidine disodium salt.

15. The compound according to claim 14 for increasing high density lipoproteins.

16. A pharmaceutical composition comprising a compound selected from the group consisting of $N^\alpha$-glutaryl-L-histidine, $N^\alpha$-glutaryl-L-histidine monosodium salt, $N^\alpha$-glutaryl-L-histidine disodium salt, $N^\alpha$-succinyl-L-tryptophane monosodium salt, $N^\alpha$-glutaryl-L-tryptophane monosodium salt and $N^\alpha$-succinyl-L-histidine monosodium salt and a pharmaceutically acceptable additive, wherein the compound is present in an amount effective to increase high density lipoproteins.

17. A medicament for increasing high density lipoproteins comprising a compound selected from the group consisting of $N^\alpha$-glutaryl-L-histidine, $N^\alpha$-glutaryl-L-histidine monosodium salt, $N^\alpha$-glutaryl-L-histidine disodium salt, $N^\alpha$-succinyl-L-tryptophane monosodium salt, $N^\alpha$-glutaryl-L-tryptophane monosodium salt and $N^\alpha$-succinyl-L-histidine monosodium salt, wherein compound is present in an amount effective to increase high density lipoproteins.

* * * * *